(12) United States Patent
Heikenfeld

(10) Patent No.: US 10,888,244 B2
(45) Date of Patent: *Jan. 12, 2021

(54) SWEAT SENSING WITH CHRONOLOGICAL ASSURANCE

(71) Applicant: University Of Cincinnati, Cincinnati, OH (US)

(72) Inventor: Jason Charles Heikenfeld, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 258 days.

This patent is subject to a terminal disclaimer.

(21) Appl. No.: 16/192,862

(22) Filed: Nov. 16, 2018

(65) Prior Publication Data

US 2019/0082999 A1 Mar. 21, 2019

Related U.S. Application Data

(63) Continuation of application No. 14/516,974, filed on Oct. 17, 2014, now Pat. No. 10,136,831.
(Continued)

(51) Int. Cl.
*A61B 5/145* (2006.01)
*A61B 5/053* (2006.01)
(Continued)

(52) U.S. Cl.
CPC ........ *A61B 5/0531* (2013.01); *A61B 5/14517* (2013.01); *A61B 5/14521* (2013.01);
(Continued)

(58) Field of Classification Search
CPC .......... A61B 5/053; A61B 10/00; A61B 5/00; A61B 5/145; A61B 5/7292; A61B 5/4266;
(Continued)

(56) References Cited

U.S. PATENT DOCUMENTS 4,190,060 A 2/1980 Greenleaf et al.
4,542,751 A 9/1985 Webster et al.
(Continued)

FOREIGN PATENT DOCUMENTS

CA 2869469 A1 10/2013
CN 1874720 A 12/2006
(Continued)

OTHER PUBLICATIONS

Australian Patent Office, Patent Examination Report No. 1 issued in Australian Application No. 2013243541 dated Nov. 25, 2016, 4 pages.
(Continued)

*Primary Examiner* — Eric J Messersmith
(74) *Attorney, Agent, or Firm* — Wood Herron & Evans LLP

(57) ABSTRACT

Devices that sense sweat and are capable of providing chronological assurance are described. The device uses at least one sensor to measure sweat or its components and to determine a sweat sampling rate. The chronological assurance is determined, at least in part, using the sweat sampling rate. The sweat sampling rate may be determined, at least in part, using a sweat volume and/or a sweat generation rate, both of which may be measured or predetermined.

20 Claims, 4 Drawing Sheets

Related U.S. Application Data

(60) Provisional application No. 61/892,859, filed on Oct. 18, 2013.

(51) Int. Cl.

| | | |
|---|---|---|
| *A61B 5/00* | (2006.01) | |
| *A61B 10/00* | (2006.01) | |
| *A61N 1/32* | (2006.01) | |
| *A61B 18/12* | (2006.01) | |
| *A61B 18/00* | (2006.01) | |
| *A61N 1/04* | (2006.01) | |

(52) U.S. Cl.
CPC ............ *A61B 5/4266* (2013.01); *A61B 5/443* (2013.01); *A61B 5/7221* (2013.01); *A61B 5/7292* (2013.01); *A61B 10/0064* (2013.01); *A61N 1/325* (2013.01); *A61B 2018/00654* (2013.01); *A61B 2018/124* (2013.01); *A61B 2562/0295* (2013.01); *A61B 2562/168* (2013.01); *A61N 1/0448* (2013.01)

(58) Field of Classification Search
CPC ..... A61B 5/7221; A61B 5/0531; A61B 5/443; A61B 5/14521; A61B 5/14517; A61B 10/0064; A61B 2562/0295; A61B 2018/124; A61B 2562/168; A61B 2018/00654; A61N 1/325; A61N 1/0448
See application file for complete search history.

(56) References Cited

U.S. PATENT DOCUMENTS

| | | |
|---|---|---|
| 4,756,314 A | 7/1988 | Eckenhoff et al. |
| 4,820,263 A | 4/1989 | Spevak et al. |
| 5,036,861 A | 8/1991 | Sembrowich et al. |
| 5,050,604 A | 9/1991 | Reshef et al. |
| 5,140,985 A | 8/1992 | Schroeder et al. |
| 5,246,003 A | 9/1993 | DeLonzor |
| 5,438,984 A | 8/1995 | Schoendorfer |
| 5,556,789 A | 9/1996 | Goerlach-Graw et al. |
| 5,814,599 A | 9/1998 | Mitragotri et al. |
| 5,944,662 A | 8/1999 | Schoendorfer |
| 6,198,953 B1 | 3/2001 | Webster et al. |
| 6,256,533 B1 | 7/2001 | Yuzhakov et al. |
| 6,269,265 B1 | 7/2001 | Anderson |
| 6,299,578 B1 | 10/2001 | Kurnik et al. |
| 6,592,529 B2 | 7/2003 | Marett |
| 6,666,821 B2 | 12/2003 | Keimel |
| 7,190,986 B1 | 3/2007 | Hannula et al. |
| 7,219,534 B2 | 5/2007 | Campbell |
| 7,378,054 B2 | 5/2008 | Karmali |
| 7,383,072 B2 | 6/2008 | Edmonson et al. |
| 7,384,396 B2 | 6/2008 | Samuels et al. |
| 7,749,445 B2 | 7/2010 | Masters |
| 7,813,780 B2 | 10/2010 | Shah et al. |
| 7,842,234 B2 | 11/2010 | Lauks et al. |
| 7,959,791 B2 | 6/2011 | Kjaer et al. |
| 8,125,539 B2 | 2/2012 | Takashima |
| 8,128,889 B2 | 3/2012 | Fujimoto et al. |
| 8,252,248 B2 | 8/2012 | Kramer |
| 8,391,946 B2 | 3/2013 | Sugenoya et al. |
| 8,565,850 B2 | 10/2013 | Martinsen et al. |
| 8,593,287 B2 | 11/2013 | Hayter et al. |
| 8,617,067 B2 | 12/2013 | Jain et al. |
| 9,133,024 B2 | 9/2015 | Phan et al. |
| 2002/0091312 A1 | 7/2002 | Berner et al. |
| 2003/0135100 A1 | 7/2003 | Kim et al. |
| 2003/0191376 A1 | 10/2003 | Samuels et al. |
| 2003/0201194 A1 | 10/2003 | Heller et al. |
| 2004/0249310 A1 | 12/2004 | Shartle et al. |
| 2004/0267189 A1 | 12/2004 | Mavor et al. |
| 2005/0069925 A1 | 3/2005 | Ford et al. |
| 2005/0106713 A1 | 5/2005 | Phan et al. |
| 2005/0177035 A1 | 8/2005 | Botvinick et al. |
| 2005/0192528 A1 | 9/2005 | Tapper |
| 2005/0197554 A1 | 9/2005 | Polcha |
| 2006/0004271 A1 | 1/2006 | Peyser et al. |
| 2006/0062852 A1 | 3/2006 | Holmes |
| 2006/0127964 A1 | 6/2006 | Ford et al. |
| 2006/0253011 A1 | 11/2006 | Edmonson et al. |
| 2006/0254341 A1 | 11/2006 | Campbell |
| 2007/0027383 A1* | 2/2007 | Peyser ................ A61B 5/1486 600/347 |
| 2007/0032731 A1 | 2/2007 | Lovejoy et al. |
| 2007/0179371 A1 | 8/2007 | Peyser et al. |
| 2008/0015494 A1 | 1/2008 | Santini et al. |
| 2008/0045816 A1 | 2/2008 | Jang et al. |
| 2008/0154179 A1 | 6/2008 | Cantor et al. |
| 2008/0286349 A1 | 11/2008 | Nomoto et al. |
| 2008/0306362 A1 | 12/2008 | Davis |
| 2009/0076345 A1 | 3/2009 | Manicka et al. |
| 2009/0204008 A1 | 8/2009 | Beilin |
| 2009/0270704 A1 | 10/2009 | Peyser et al. |
| 2010/0044224 A1 | 2/2010 | Kataky |
| 2010/0063372 A1* | 3/2010 | Potts ................ A61B 5/14521 600/346 |
| 2010/0130843 A1 | 5/2010 | Caceres Galvez et al. |
| 2010/0132485 A1 | 6/2010 | Erez et al. |
| 2010/0179403 A1 | 7/2010 | Martinsen et al. |
| 2010/0198521 A1 | 8/2010 | Haick |
| 2010/0234712 A1 | 9/2010 | Sugenoya et al. |
| 2011/0079521 A1 | 4/2011 | Revol-Cavalier |
| 2011/0118656 A1 | 5/2011 | Eckhoff et al. |
| 2011/0178380 A1 | 7/2011 | Chowdhury |
| 2011/0196283 A1 | 8/2011 | Imran et al. |
| 2011/0208458 A1 | 8/2011 | Pinter et al. |
| 2011/0275918 A1 | 11/2011 | Yamashita et al. |
| 2012/0004570 A1 | 1/2012 | Shimizu et al. |
| 2012/0028283 A1 | 2/2012 | Floss et al. |
| 2012/0123220 A1 | 5/2012 | Iyer et al. |
| 2012/0165626 A1 | 6/2012 | Irina et al. |
| 2012/0209226 A1 | 8/2012 | Simmons et al. |
| 2012/0229661 A1 | 9/2012 | Sekiguchi et al. |
| 2012/0277697 A1 | 11/2012 | Haghgooie et al. |
| 2012/0285829 A1 | 11/2012 | Mount et al. |
| 2012/0317430 A1 | 12/2012 | Rahman et al. |
| 2012/0323097 A9 | 12/2012 | Chowdhury |
| 2013/0006079 A1 | 1/2013 | Feldman et al. |
| 2013/0010108 A1 | 1/2013 | Hashizume et al. |
| 2013/0013028 A1 | 1/2013 | Kriksunov et al. |
| 2013/0053668 A1 | 2/2013 | Lin |
| 2013/0079605 A1 | 3/2013 | Bandaru et al. |
| 2013/0099937 A1 | 4/2013 | Azimi |
| 2013/0108667 A1 | 5/2013 | Soikum et al. |
| 2013/0123595 A1 | 5/2013 | Currie et al. |
| 2013/0183399 A1 | 7/2013 | Blow |
| 2013/0245388 A1 | 9/2013 | Rafferty et al. |
| 2013/0306491 A1 | 11/2013 | Briman et al. |
| 2013/0317333 A1 | 11/2013 | Yang et al. |
| 2014/0012114 A1 | 1/2014 | Zevenbergen et al. |
| 2014/0025000 A1 | 1/2014 | Currie et al. |
| 2014/0206977 A1 | 7/2014 | Bahney et al. |
| 2014/0275862 A1 | 9/2014 | Kennedy |
| 2014/0276220 A1 | 9/2014 | Briscoe et al. |
| 2014/0343371 A1 | 11/2014 | Sowers, II et al. |
| 2015/0057515 A1 | 2/2015 | Hagen et al. |
| 2015/0112164 A1 | 4/2015 | Heikenfeld et al. |
| 2015/0112165 A1 | 4/2015 | Heikenfeld |
| 2016/0058354 A1 | 3/2016 | Phan et al. |
| 2016/0066828 A1 | 3/2016 | Phan et al. |
| 2016/0157768 A1 | 6/2016 | Braig et al. |

FOREIGN PATENT DOCUMENTS

| | | |
|---|---|---|
| CN | 1969184 A | 5/2007 |
| CN | 1984716 A | 6/2007 |
| CN | 101380240 A | 3/2009 |
| CN | 101489470 A | 7/2009 |
| CN | 201508360 U | 6/2010 |
| EP | 0282349 A2 | 9/1988 |
| EP | 0453283 A1 | 10/1991 |
| EP | 0634215 A1 | 1/1995 |
| EP | 1500937 A1 | 1/2005 |

(56) References Cited

FOREIGN PATENT DOCUMENTS

| | | |
|---|---|---|
| EP | 1637889 A1 | 3/2006 |
| EP | 2551784 A1 | 1/2013 |
| JP | H07-77525 A | 3/1995 |
| JP | H08-504513 A | 5/1996 |
| JP | 2007503958 A | 3/2007 |
| JP | 2007532260 A | 11/2007 |
| JP | 2008505330 A | 2/2008 |
| JP | 200963597 A | 3/2009 |
| JP | 2009118420 A | 5/2009 |
| WO | 9011519 A1 | 10/1990 |
| WO | 9414062 A1 | 6/1994 |
| WO | 0014535 A1 | 3/2000 |
| WO | 01/88525 A1 | 11/2001 |
| WO | 2006133101 A2 | 12/2006 |
| WO | 2007097754 A1 | 8/2007 |
| WO | 2007146047 A1 | 12/2007 |
| WO | 2008083687 A1 | 7/2008 |
| WO | 2008095940 A1 | 8/2008 |
| WO | 2009004001 A1 | 1/2009 |
| WO | 2009052321 A2 | 4/2009 |
| WO | 2010017578 A1 | 2/2010 |
| WO | 2011117952 A1 | 9/2011 |
| WO | 2013152087 A2 | 10/2013 |
| WO | 2013181436 A1 | 12/2013 |
| WO | 2014001577 A1 | 1/2014 |
| WO | 2014025430 A2 | 2/2014 |
| WO | 2015184072 A1 | 12/2015 |
| WO | 2015184097 A2 | 12/2015 |
| WO | 2016049019 A1 | 3/2016 |
| WO | 2016061362 A2 | 4/2016 |
| WO | 2016090189 A1 | 6/2016 |
| WO | 2016130905 A1 | 8/2016 |
| WO | 2016138087 A1 | 9/2016 |
| WO | 2017019602 A1 | 2/2017 |
| WO | 2017070640 A1 | 4/2017 |

OTHER PUBLICATIONS

Australian Patent Office, Notice of Acceptance for Patent Applicatin issued in Australian Application No. 2013243541 dated Mar. 23, 2017 (3 pages).

Chinese Patent Office, First Office Action issued in Chinese Application No. 201380028053.8 dated Dec. 21, 2105, 4 pages.

Chinese Patent Office, Second Office Action issued in Chinese Application No. 201380028053.8 dated Sep. 20, 2016, 8 pages (including English language translation).

Chinese Patent Office, Third Office Action issued in Chinese Application No. 201380028053.8 dated Mar. 20, 2017, 17 pages (including English language translation).

European Patent Office, Written Opinion of the International Search Authority / International Preliminary Report on Patentability for PCT/US2013/035092 dated Oct. 16, 2014 (14 pages).

European Patent Office, Partial European Search Report issued in European Application No. 16203346.8-1657 dated Mar. 24, 2017, 7 pages.

Fu et al., "Controlled Reagent Transport in Disposable 2D Paper Networks", The Royal Society of Chemistry 2010, Lab Chip, 2010, 10, 918-920.

International Searching Authority, Search Report and Written Opinion issued in corresponding International Application No. PCT/US2014/061098 dated Dec. 12, 2014, 13 pages.

International Searching Authority, Invitation to Pay Additional Search Fees and, Where Applicable, Protest Fee, and Communication Relating to the Results of the Partial International Search, issued in International Application No. PCT/US2014/061083 dated Dec. 15, 2014, 6 pages.

International Searching Authority, Search Report and Written Opinion issued in International Application No. PCT/US2014/061083 dated Mar. 31, 2015, 18 pages.

International Searching Authority, Search Report and Written Opinion issued in International Application No. PCT/US2015/032830 dated Aug. 14, 2015, 9 pages.

International Searching Authority, Search Report and Written Opinion issued in International Application No. PCT/US2015/032843 dated Oct. 26, 2015, 11 pages.

International Searching Authority, Search Report and Written Opinion issued in International Application No. PCT/US2015/032866 dated Nov. 19, 2015, 12 pages.

International Searching Authority, Search Report and Written Opinion issued in International Application No. PCT/US2015/032893 dated Nov. 13, 2015, 14 pages.

International Searching Authority, Search Report and Written Opinion issued in International Application No. PCT/US2015/040113 dated Feb. 4, 2016, 13 pages.

International Searching Authority, Search Report and Written Opinion issued in International Application No. PCT/US2015/051439 dated Dec. 28, 2015, 7 pages.

International Searching Authority, Invitation to Pay Additional Search Fees and, Where Applicable, Protest Fee, and Communication Relating to the Results of the Partial International Search, issued in International Application No. PCT/US2015/032843 dated Aug. 18, 2015, 2 pages.

International Searching Authority, Invitation to Pay Additional Search Fees and, Where Applicable, Protest Fee, and Communication Relating to the Results of the Partial International Search, issued in International Application No. PCT/US2015/040113 dated Dec. 1, 2015, 2 pages.

International Searching Authority, Invitation to Pay Additional Search Fees and, Where Applicable, Protest Fee, and Communication Relating to the Results of the Partial International Search, issued in International Application No. PCT/US2015/032866 dated Aug. 31, 2015, 2 pages.

International Searching Authority, Invitation to Pay Additional Search Fees and, Where Applicable, Protest Fee, and Communication Relating to the Results of the Partial International Search, issued in International Application No. PCT/US2015/032893 dated Aug. 31, 2015, 2 pages.

International Searching Authority, Search Report and Written Opinion issued in International Application No. PCT/US16/18635 dated May 6, 2016, 12 pages.

International Searching Authority, Search Report and Written Opinion issued in International Application No. PCT/US16/17726 dated May 12, 2016, 9 pages.

International International Bureau, Notification Concerning Transmittal of International Preliminary Report on issued in International Application No. PCT/US13/35092 dated Oct. 16, 2014, 14 pages.

International Searching Authority, Invitation to Pay Additional Fees and, Where Applicable, Protest Fee, and Communication Relating to the Results of the Partial International Search, issued in International Application No. PCT/US13/35092 dated Aug. 26, 2013, 9 pages.

International Searching Authority, Search Report and Written Opinion issued in International Application No. PCT/US16/59392 dated Oct. 28, 2016, 13 pages.

International Searching Authority, Search Report and Written Opinion issued in International Application No. PCT/US16/50928 dated Sep. 9, 2016, 8 pages.

International Searching Authority, Search Report and Written Opinion issued in International Application No. PCT/US16/43862 dated Oct. 19, 2016, 14 pages.

International Searching Authority, Search Report and Written Opinion issued in International Application No. PCT/US2017/013453 dated May 18, 2017, 14 pages.

International Searching Authority, Search Report and Written Opinion issued in International Application No. PCT/US2017/039421 dated Sep. 6, 2017, 10 pages.

International Searching Authority, Search Report and Written Opinion issued in International Application No. PCT/US2017/040588 dated Sep. 25, 2017, 11 pages.

Japanese Patent Office, Office Action issued in Japanese Application No. 2015-504702 dated Jan. 20, 2017, 7 pages (including English language translation).

Stoppa, Matteo, et. al., "Wearable Electronics and Smart Tectiles: A Critical Review," Sensors, 2014, pp. 11957-11992, vol. 14 (36 pages).

(56) References Cited

OTHER PUBLICATIONS

European Patent Office, Supplemental European Search Report issued in European Application No. 15799514.3-1657 dated Dec. 7, 2017, 8 pages.
European Patent Office, Supplemental European Search Report issued in European Application No. 15799317.1-1657 dated Dec. 21, 2017, 9 pages.
European Patent Office, Partial European Search Report issued in European Application No. 15800043.0-115 dated Jan. 8, 2018, 13 pages.
International Searching Authority, Search Report and Written Opinion issued in International Application No. PCT/US2017/047574 dated Nov. 16, 2017, 14 pages.
International Searching Authority, Search Report and Written Opinion issued in International Application No. PCT/US2017/052651 dated Dec. 12, 2017, 14 pages.
Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.
Sonner, Z., et al., "The microfluidics of the eccrine sweat gland, including biomarker partitioning, transport, and biosensingi implications,"Biomicrofluidics, vol. 9, pp. 031301-1-031301-19, CrossMark, 19 pages.
International Searching Authority, Search Report and Written Openin in International Application No. PCT/US2016/043862, dated Oct. 19, 2016 (14 pages).
European Patent Office, Official Communication for EP Application No. 13 718 933.8-1101 dated Feb. 14, 2018 (5 pages).
European Patent Office, Extended European Search Report issued in European Application No. 15819306.0-1115 dated Feb. 9, 2018 (9 pages).
International Searching Authority, Search Report and Written Opinion issued in International Application No. PCT/US20171067495 dated Mar. 1, 2018, 10 pages.
International Searching Authority/US, International Search Report and Written Opinion issued in corresponding PCT Application No. PCT/US2016/059392, dated Feb. 15, 2017 (12 pages).
European Patent Office, Extended Search Report issued in European Application No. 15844313.5 dated Mar. 15, 2018, 15 pages.
De Jong, J. et al., "Membranes and microfluidics: a review," Lab Chip, 2006, 6, 1125-1139 (15 pages).
Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.
European Patent Office, Extended Search Report issued for European Application No. 15800043.0-1115 dated Apr. 16, 2018, 11 pages.
Agwuh, Kenneth N., et al., "Pharmacokinetics and pharmacodynamics of the tetracyclines including glycylcyclines," Journal of Antimicrobial Chemotherapy, 2006, vol. 58, pp. 256-265, Advance Access Publication (10 pages).
Argatroban Injection, Package Insert for Argatroban Injection, "Highlights of Prescribing Information," Research Triangle Park, NC, GlaxoSmithKline, 2012 (22 pages).
Balant-Gorgia, Androniki E., et al., "Clinical Pharmacokinetics of Clompipramine," Clin. Pharmacokinet., vol. 20 (6), 1991, pp. 447-462 (16 pages).
Baxter, Roger, et al., "Comparison of Bactericidal Activity of Five Antibiotics against *Staphylococcus aureus*," Oxford Journals, The Journal of Infectious Diseases, vol. 161, No. 5, May 1990, pp. 1023-1025, Oxford University Press (4 pages).
Bertrand, Julie, et al., "Influence of pharmacogenetics on indinavir dispostion and short-term response in HIV patients initiating HAART," Eur J Clin Pharmacol., Jul. 22, 2010, vol. 65(7), pp. 667-678 (17 pages).
Bockbrader, Howard N., et al., "Clinical Pharmacokinetics of Pregabalin in Healthy Volunteers," Journal of Clinical Pharmacology, 2010, vol. 50, pp. 941-950 (10 pages).

Buch, A.B., et al., "A Study of Pharmacokinetic Interaction Between Buspirone and Alprazolam at Steady State," J Clin Pharmacol, 1993, vol. 33, pp. 1104-1109 (6 pages).
Fonseca, Walter, et al., "Comparing Pharmacokinetics of Amoxicillin Given Twice or Three Times per Day to Children Older than 3 Months with Pneumonia," Antimicrobial Agents and Chemotherapy, Mar. 2003, vol. 47, No. 3, pp. 997-1001, American Society for Microbiology (5 pages).
Friedrich, Lawrance V., et al., "Aztreonam Pharmacokinetics in Burn Patients," Antimicrobial Agents and Chemotherapy, Jan. 1991, vol. 35, No. 1, pp. 57-61, American Society for Microbiology (5 pages).
Garcia, David A., et al., "Parenteral Anticoagulants: Antithrombotic Therapy and Prevention of Thrombosis, 9th ed: American College of Chest Physicians Evidence-Based Clinical Practice Guidelines," Chest, 2012, vol. 141/2 (Supplement), pp. e24S-e43S (20 pages).
Geller, David E., et al., :Pharmacokinetics and Bioavailability of Aerosolized Tobramycin in Cystic Fibrosis, Chest, vol. 122, No. 1, Jul. 2002, pp. 219-226 (8 pages).
Glazer, William M., et al., "The determination of the steady-state pharmacokinetic profile of fluphenazine decanoate by gas chromatography/mass spectrometry detection," Schizophrenia Research, 1992, vol. 8, pp. 111-117, Elsevier Science Publishers B.V. (7 pages).
Goodwin, Megan L., et al., "Antifungal serum concentration monitoring: an update," Journal of Antimicrobial Chemotherapy, 2008, vol. 61, pp. 17-25, Advance Access publicaiton Nov. 12, 2007 (9 pages).
Hsu, Ann, et al., "Multiple-Dose Pharmacokinetics of Ritonavir in Human Immunodeficiency Virus-Infected Subjects," Antimicrobial Agents and Chemotherapy, May 1997, Vo. 41, No. 5, pp. 898-905, American Society for Microbiology (8 pages).
Hyland, R., et al., "Identification of the Cytochrome P450 Enzymes Involved in the N-Oxidation of Voriconazole," Drug Metabolism and Disposition, Jan. 2003, vol. 31, No. 5, pp. 540-547, The American Society for Pharmacology and Experimental Therapeutics (8 pages).
Kappelhoff, Bregt S., et al., "Pharmacokinetics of Nevirapine: Once-Daily Versus Twice-Daily Dosing in the 2NN Study," HIV Clinical Trials, Sep. 2005, vol. 6(5), pp. 254-261, Thomas Land Publishers, Inc. (9 pages).
La Porte, C.J.L., et al., "Pharmacokinetics of Adjusted-Dose Lopinavir-Ritonavir Combined with Rifampin in Healthy Volunteers," Antimicrobial Agents and Chemotherapy, May 2004, vol. 48, No. 5, pp. 1553-1560, American Society for Microbiology (8 pages).
Lacy, Melinda K., et al., "Comparison of bactericidal activity after multidose administration of clarithromycin, azithromycin, and cefuroxime axetil aginst *Streptococcus pneumoniae*," International Journal of Antimicrobial Agents 10, 1998, pp. 279-283, Elsevier (5 pages).
Lai, Allen A., et al., "Time-course of interaction between carbamazepine and clonazepam in normal man," Clin. Pharmacol. Ther, Sep. 1978, vol. 24, pp. 316-323, The C.V. Mosby Co. (8 pages).
Marshall, William F., et al., "The Cephalosporins," Symposium on Antimicrobial Agents—Part V, Mayo Clin Proc, 1999, vol. 74, pp. 187-195 (9 pages).
McIlleron, Helen, et al., "Determinants of Rifampin, Isoniazid, Pyrazinamide, and Ethambutol Pharmacokinetics in a Cohort of Tuberculosis Patients," Antimicrobial Agents and Chemotherapy, Apr. 2006, vol. 50, No. 4, pp. 1170-1177, American Society for Microbiology (8 pages).
Medscape, "Drug, OTCs and Herbals | Medscape Reference," http://www.reference.medscapte.com/drugs, Accessed Mar. 2013 and Apr. 3, 2017 (1 page).
Mimaki, Takashi, "Clinical Pharmacology and Therapeutic Drug Monitoring of Zonisamide," Therapeutic Drug Monitoring, Dec. 1998, vol. 20(6), pp. 593-597, Lippincott Williams & Wilkins, Inc. (9 pages).
Molina, J-M., et al., "Pharmacokinetics of emtricitabine, didanosine andefavirenz administered once-daily for the treatment of HIV-infected adults (Pharmacokinetic substudy of the ANRS 091 trial)," HIV Medicine (2004), vol. 5, pp. 39-104, 2004 British HIV Association (6 pages).

(56) References Cited

OTHER PUBLICATIONS

Morse, Gene D., et al., "Multiple-Dose Pharmacokinetics of Delavirdine Mesylate and Didanosine in HIV-Infected Patients," Clin Drug Invest, 2003, pp. 323-328, vol. 23 (5), Adis Data Information BV (6 pages).
Munne P. International Programme on Chemical Safety Poisons Information Monograph 181, "Pharmacology and Toxicology," Published Apr. 1990, available at: http://www.inchem.org/documents/pims/pharm/pim181.htm#PartTitle:7.%20%20PHARMACOLOGY%20AND%20TOXICOLOGY, Accessed Oct. 2, 2009, pp. 14-18 (5 pages).
Vauta, Ernst H., et al., "Dicloxacillin and cloxacillin: Pharmacokinetics in healthy and hemodialysis subjects," Clinical Pharmacology and Therapeutics, vol. 20, No. 1, Feb. 13, 1976, pp. 98-108 (11 pages).
Ochs, Hermann R., et al., "Digitoxin Accumulation," Br. J. clin. Pharmac. (1982), vol. 14, pp. 225-229. The Macmillan Press Ltd 1982 (5 pages).
Ordonez Gallego, A., et al., "Oxycodone: a pharmacological and clinical review," Clin Transl Oncol, 2007, vol. 9, pp. 298-307 (10 pages).
Pippenger, C.E., et al., "Principles of Therapeutic Drug Monitoring," In: Wong Shy, ed. Therapeutic Drug Monitoring and Toxicology by Liquid Chromatography. Boca Raton, FL: CRC Press, 1985, pp. 11-36 (26 pages).
Purkins, L., et al., "Pharmacokinetics and Safety of Voriconazole following Intravenous-to Oral-Dose Escalation Regimens," Antimicrobial Agents and Chemotherapy, Aug. 2002, vol. 46, No. 8, pp. 2546-2553, American Society for Microbiology (8 pages).
Purkins, Lynn, et al., "The pharmacokinetics and safety of intravenous voriconazole—a novel wide-spectrum antifungal agent," Br J Clin Pharmacol, 2003, vol. 56, pp. 2-9, Blackwell Publishing Ltd (8 pages).
Ratjen, F., et al., "Pharmacokinetics of inhaled colistin in patients with cystic fibrosis," Journal of Antimicrobial Chemotherapy, 2006, vol. 57, pp. 306-311 (6 pages).
Remmel, Rory P., et al., "Simultaneous Assay of Felbamate plus Carbamazepine, Phenytoin, and Their Metabolites by Liquid Chromatography with Mobile Phase Optimization," Therapeutic Drug Monitoring, 1990, vol. 12, pp. 90-96, Raven Press, Ltd., New York (7 pages).
Rosenfeld, W.E, et al., "Comparison of the Steady-State Pharmacokinetics of Topiramate and Valproate in Patients with Epilepsy During Monotherapy and Concomitant Therapy," Epilepsia, 1997, vol. 38(3), pp. 324-333, Lippincott-Raven Publishers, Philadelphia (10 pages).
Ruslami, Rovina, et al., "Pharmacokinetics and Tolerability of a Higher Rifampin Dose versus the Standard Dose in Pulmonary Tuberculosis Patients," Antimicrobial Agents and Chemotherapy, Jul. 2007, vol. 51, No. 7, pp. 2546-2551, American Society for Microbiology (6 pages).
Rythmol, Package Insert for Rythmol, "Highlights of Prescribing Information," Reliant Pharmaceuticals Inc., 2004 (24 pages).
Sadler, Brian M., et al., "Pharmacokinetic and Pharmacodynamic Study of the Human Immunodeficiency Virus Protease Inhibitor Amprenavir after Multiple Oral Dosing," Antimicrobial Agents and Chemotherapy, Jan. 2001, vol. 45, No. 1, pp. 30-37, American Society for Microbiology (8 pages).
Silverstein, Jeffrey H., et al., "An Analysis of the Duration of Fentanyl and Its Metabolites in Urine and Saliva," Anesth Analg, 1993, vol. 76:6, pp. 618-621, The International Anesthesia Research Society (4 pages).
Sobue, Satoshi, et al., "Pharmacokinetics of fosfluconzaole and fluconazole following multiple intravenous administration of fosfluconazole in healthy male volunteers," British Journal of Clinical Pharmacology, 2004, vol. 58:1, pp. 20-25, Blackwell Publishing Ltd. (6 pages).
Ti, Teow-Yee, et al., "Disposition of Intravenous Metronidazole in Asian Surgical Patients," Antimicrobial Agents and Chemotherapy, Oct. 1996, vol. 40, No. 10, pp. 2248-2251, American Society for Microbiology (4 pages).
Viracept, Package Insert for Viracept, "Highlights of Prescribing Information," Agouron Pharmaceuticals, 2008 (27 pages).
Von Hentig, Nils, et al., "Pharmacokinetics of Saquinavir, Atazanavir, and Ritonavir in a Twice-Daily Boosted Double-Protease Inhibitor Regimen," Antimicrobial Agents and Chemotherapy, Apr. 2007, vol. 51, No. 4, pp. 1431-1439, American Society for Microbiology (9 pages).
Wilens, Timothy E., et al., "Fluoxetine Pharmacokinetics in Pediatric Patients," Journal of Clinical sychopharmacology, 2002, vol. 22, No. 6, pp. 568-575, Lippincott Williams & Wilkins, Inc. (8 pages).
Wong, Steven H.Y., "Therapeutic Drug Monitoring and Toxicology by Liquid Chromatography," Chromatographic Science Series, 1985, vol. 32, Chapter 2 "Principles of Therapeutic Drug Monitoring" by C.E. Pippenger, Marcel Dekker, Inc., New York and Basel (34 pages).
Yamamoto, Takatsugu, et al., "Pharmacokinetic Characteristics of Minocycline in Debilitated Elderly Patients," American Journal of Therapeutics, 1999, vol. 6, pp. 157-160 (4 pages).
Zyprexa Relprevv, Package Insert for Zyprexa Relprevv, "Highlights of Prescribing Information," Eli Lilly and Company, 2008 (27 pages).
International Bureau, Notification Concerning Transmittal of International Preliminary Report on International issued in International Application No. PCT/US13/35092, 14 pages.
International Searching Authority, Invitation to Pay Additional Fees and, Where Applicable, Protest Fee, and Communication Relating to the Results of the Partial International Search, issued in International Application No. PCT/US13/35092, 9 pages.
Chinese Patent Office, English translation of Office Action issued in corresponding Chinese Application No. 201480067960.8, dated Dec. 11, 2018, 3 pages.
International Searching Authority, Search Report and Written Opinion issued in International Application No. PCT/US2017/067495 dated Mar. 1, 2018, 10 pages.
European Patent Office, Supplementary European Search Report issued in corresponding European Application No. EP 16749949, dated Jun. 15, 2018 (7 pages).
European Patent Office, Extended European Search Report issued in corresponding European Application No. 16753129.2, dated Jun. 15, 2018 (8 pages).
European Patent Office, Extended European Search Report issued in corresponding European Application No. 15800539.7, dated Aug. 17, 2018 (6 pages).

\* cited by examiner

SWEAT SENSING WITH CHRONOLOGICAL ASSURANCE

CROSS-REFERENCE TO RELATED APPLICATIONS

This application is a continuation of U.S. patent application Ser. No. 14/516,974, filed Oct. 17, 2014, and claims the benefit of U.S. Provisional Applications No. 61/892,859, filed Oct. 18, 2013, 62/003,675, filed May 28, 2014, 62/003,707, filed May 28, 2014, and 62/023,233, filed Jul. 11, 2014, the disclosures of which are hereby incorporated by reference herein in their entirety. The present application has a specification that builds upon PCT/US13/35092, the disclosure of which is hereby incorporated herein by reference in its entirety.

STATEMENT REGARDING FEDERALLY SPONSORED RESEARCH OR DEVELOPMENT

This invention was made with government support under FA8650-09-D-5037 awarded by AFMCLO/JAZ. The government has certain rights in the invention.

BACKGROUND OF THE INVENTION

Sweat sensing technologies have enormous potential for applications ranging from athletics, to neonates, to pharmacological monitoring, to personal digital health, to name a few applications. Sweat contains many of the same biomarkers, chemicals, or solutes that are carried in blood and can provide significant information enabling one to diagnose ailments, health status, toxins, performance, and other physiological attributes even in advance of any physical sign. Furthermore, sweat itself, the action of sweating, and other parameters, attributes, solutes, or features on, near, or beneath the skin can be measured to further reveal physiological information.

If sweat has such significant potential as a sensing paradigm, then why has it not emerged beyond decades-old usage in infant chloride assays for Cystic Fibrosis or in illicit drug monitoring patches? In decades of sweat sensing literature, the majority of medical literature utilizes the crude, slow, and inconvenient process of sweat stimulation, collection of a sample, transport of the sample to a lab, and then analysis of the sample by a bench-top machine and a trained expert. This process is so labor intensive, complicated, and costly that in most cases, one would just as well implement a blood draw since it is the gold standard for most forms of high performance biomarker sensing. Hence, sweat sensing has not emerged into its fullest opportunity and capability for biosensing, especially for continuous or repeated biosensing or monitoring. Furthermore, attempts at using sweat to sense "holy grails" such as glucose have not yet succeeded to produce viable commercial products, reducing the publically perceived capability and opportunity space for sweat sensing.

Products on the market, such as one-time Cystic Fibrosis testing devices, or continuous sweat sampling and sensing devices, fail to provide chronological assurance, which is an assurance of the sampling rate for measurement(s) of sweat or solutes in sweat in terms of the rate at which measurements can be made of new sweat or its new solutes as originating from the body. Simple one-time sampling products exist where the only critical parameter is to collect an adequate sample for transfer to a chloride sensor and to preserve the sweat volume (little or no evaporation) to prevent changes in concentration of chloride in sweat. Glucose sensors may use a "fixed volume reservoir" to obtain a precise volume of sweat, which can then ensure adequate sample and to provide a more accurate determination of glucose concentration. Devices intended to test for Cystic Fibrosis in neonates, who provide very little sweat for a sample, can include a sweat generation rate measurement and a digital display of time elapsed to indicate when proper sample volume is achieved. These "continuous monitoring" devices are capable of assuring continuous sampling and reading, but not chronological assurance. This inability to provide chronological assurance is a major deficiency for many applications possible for sweat sensing.

Of all the other physiological fluids used for bio monitoring (e.g. blood, urine, saliva, tears), sweat has arguably the most variable sampling rate as its collection methods and variable rate of generation both induce large variances in the effective sampling rate. Sweat is also exposed to numerous contamination sources, which can distort the effective sampling rate. The variable sampling rate creates a challenge in providing chronological assurance, especially so in continuous monitoring applications.

For example, consider the difficulty of sampling sweat in a sweat sensing patch with a large sweat volume that could mix up sweat previously generated with the newly generated sweat that is intended to be measured to represent a measurement of sweat solutes in real time or near real time. Such need for chronological assurance is largely unique to sweat. Furthermore, even technologies useful for chronological assurance with other biofluids could be largely irrelevant as they do not work with the unique signatures of sweat and of sweat sensors that could allow for chronological assurance. Techniques exist that reduce the sweat volume, but reducing the sweat volume does not enable an understanding of how the sweat sampling rate changes with sweat volume or movement of sweat fluid or solutes between the sensors and the skin, due to diffusion, and due to sweat or flow rates. There is a clear difference between merely improving sweat volume or sweat sampling rate and providing chronological assurance.

A sweat sensor with chronological assurance is clearly needed. A continuously monitoring or one time sweat sensor might give you a biomarker reading, but if it does not tell the window over which that biomarker collection is integrated, then the reading is useless for numerous applications. For example, consider athlete monitoring during a game, the coach would want to know if the readings of fatigue on a particular athlete represent 5 minute chronological assurance or 50 minute chronological assurance. Furthermore, some biomarkers disappear from sweat in as little as 10 to 20 minutes, and an assurance that chronological readings are less than 5 to 10 minutes would be needed.

Many of the drawbacks stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sweat sensing technology into intimate proximity with sweat as it is generated. With such a new invention, sweat sensing could become a compelling new paradigm as a biosensing platform.

SUMMARY OF THE INVENTION

The present invention provides a wearable sweat sensor device capable of chronological assurance. The device includes one or more sweat sensors. At least one of the sweat sensors has a sweat sampling rate and a chronological assurance. The device further comprises a sweat sampling rate that is determined and a chronological assurance that is determined. The chronological assurance is determined at least in part by the sweat sampling rate.

BRIEF DESCRIPTION OF THE DRAWINGS

The objects and advantages of the present invention will be further appreciated in light of the following detailed descriptions and drawings in which.

DEFINITIONS

Figure 1:
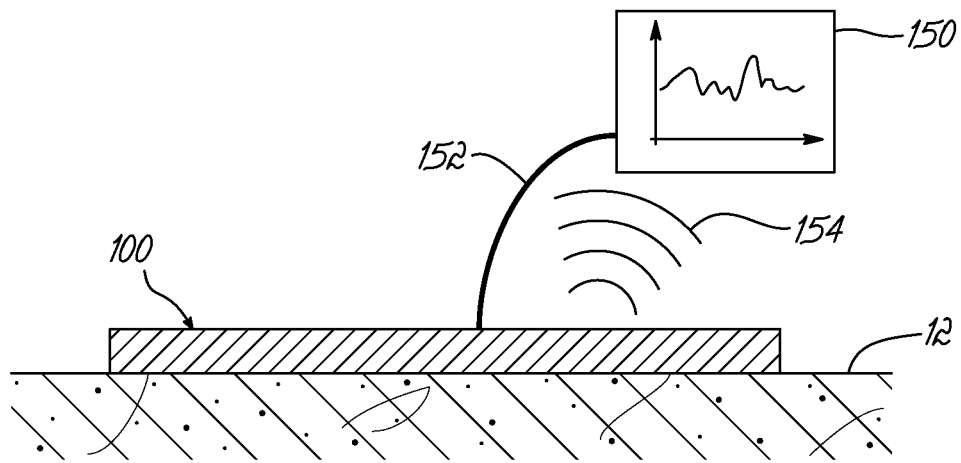
FIG. 1 is an elevation view of one embodiment of the present invention illustrating a device where the chronological assurance is reported.

As used herein, "continuous monitoring" means the capability of a device to provide at least one measurement of sweat determined by a continuous or multiple collection and sensing of that measurement or to provide a plurality of measurements of sweat over time.

As used herein, "chronological assurance" is an assurance of the sampling rate for measurement(s) of sweat or solutes in sweat in terms of the rate at which measurements can be made of new sweat or its new solutes as originating from the body. Chronological assurance may also include a determination of the effect of potential contamination with previously generated sweat, previously generated solutes, other fluid, or other measurement contamination sources for the measurement(s).

As used herein, "determined" may encompass more specific meanings including but not limited to: something that is predetermined before use of a device; something that is determined during use of a device; something that could be a combination of determinations made before and during use of a device.

As used herein, "sweat sampling rate" is the effective rate at which new sweat or sweat solutes, originating from the sweat gland or from skin or tissue, reaches a sensor which measures a property of sweat or its solutes. Sweat sampling rate, in some cases, can be far more complex than just sweat generation rate. Sweat sampling rate directly determines or is a contributing factor in determining the chronological assurance. Times and rates are inversely proportional (rates having at least partial units of 1/seconds), therefore a short or small time required to refill a sweat volume can also be said to have a fast or high sweat sampling rate. The inverse of sweat sampling rate (1/s) could also be interpreted as a "sweat sampling interval" (s). Sweat sampling rates or intervals are not necessarily regular, discrete, periodic, discontinuous, or subject to other limitations. Like chronological assurance, sweat sampling rate may also include a determination of the effect of potential contamination with previously generated sweat, previously generated solutes, other fluid, or other measurement contamination sources for the measurement(s). Sweat sampling rate can also be in whole or in part determined from solute generation, transport, advective transport of fluid, diffusion transport of solutes, or other factors that will impact the rate at which new sweat or sweat solutes reach a sensor and/or are altered by older sweat or solutes or other contamination sources.

As used herein, "sweat stimulation" is the direct or indirect causing of sweat generation by any external stimulus, the external stimulus being applied for the purpose of stimulating sweat. One example of sweat stimulation is the administration of a sweat stimulant such as pilocarpine. Going for a jog, which stimulates sweat, is only sweat stimulation if the subject jogging is jogging for the purpose of stimulating sweat.

As used herein, "sweat generation rate" is the rate at which sweat is generated by the sweat glands. Sweat generation rate is typically measured by the flow rate from each gland in nL/min/gland. In some cases, the measurement is then multiplied by the number of sweat glands from which the sweat is being sampled.

As used herein, "active control of sweat sampling rate" is where an external stimulus is applied to skin or the body to change or control the sweat generation rate and therefore the sweat sampling rate. This may also be more directly referred to as "active control of sweat generation rate."

As used herein, "measured" can imply an exact or precise quantitative measurement and can include broader meanings such as, for example, measuring a relative amount of change of something. Measured can also imply a binary measurement, such as 'yes' or 'no' type measurements.

As used herein, a "determined sweat generation rate" is one that is determined during use of a sweat measuring device.

As used herein, a "predetermined sweat generation rate" is one that is determined from a method other than during use of a sweat measuring device that uses predetermined sweat generation rate to provide chronological assurance.

As used herein, "sweat volume" is the fluidic volume in a space that can be defined multiple ways. Sweat volume may be the volume that exists between a sensor and the point of generation of sweat or a solute moving into or out of sweat from the body or from other sources. Sweat volume can include the volume that can be occupied by sweat between: the sampling site on the skin and a sensor on the skin where the sensor has no intervening layers, materials, or components between it and the skin; or the sampling site on the skin and a sensor on the skin where there are one or more layers, materials, or components between the sensor and the sampling site on the skin.

As used herein, a "predetermined sweat volume" is one that is determined before use of a sweat measuring device.

As used herein, a "determined sweat volume" is one that is determined during use of a sweat measuring device.

As used herein, "solute generation rate" is simply the rate at which solutes move from the body or other sources into sweat. "Solute sampling rate" includes the rate at which these solutes reach one or more sensors.

As used herein, "microfluidic components" are channels in polymer, textiles, paper, or other components known in the art of microfluidics for guiding movement of a fluid or at least partial containment of a fluid.

As used herein, "state void of sweat" is where a space or material or surface that can be wetted, filled, or partially filled by sweat is in a state where it is entirely or substantially (e.g. >50%) dry or void of sweat.

As used herein, "advective transport" is a transport mechanism of a substance or conserved property by a fluid due to the fluid's bulk motion.

As used herein, "diffusion" is the net movement of a substance from a region of high concentration to a region of low concentration. This is also referred to as the movement of a substance down a concentration gradient.

As used herein, "convection" is the concerted, collective movement of groups or aggregates of molecules within fluids and rheids, either through advection or through diffusion or a combination of both.

As used herein, "predetermined solute transport" is solute transport other than advective transport that is determined before use of a sweat measuring device.

As used herein, "measured solute transport" is solute transport other than advective transport that is determined during use of a sweat measuring device.

As used herein, "external input" means information, directions, or data entered into a device from an input outside the device or its specific system components (e.g. a heart rate measured by another device that is not incorporated with the device receiving the external input).

As used herein, "incorporated by data entry" means information, directions, or data entered into a device. Such data could be entered also into another device which communicates data into the device in which data is incorporated by data entry.

As used herein, "mediated by electric field" means transport of fluid or solutes in fluid by application of electric field.

DETAILED DESCRIPTION OF THE INVENTION

To understand the proper numerical values or representations of sweat sampling rate and therefore chronological assurance, sweat generation rate and sweat volumes should be understood. The number of active sweat glands varies greatly among different people, though comparisons between different areas (ex. axillae versus groin) show the same directional changes (certain areas always have more active sweat glands while others always have fewer). Estimates of the number of glands per $cm^2$ for different areas of the body include: around 370 sweat glands per $cm^2$ for the palm; 200 for the back of the hand; 175 for the forehead; 155 for the breast, abdomen, and forearm; and 60-80 for the back and legs. Assuming use of a sweat gland density of $100/cm^2$, a sensor that is 0.55 cm in radius (1.1 cm in diameter) would cover about 1 $cm^2$ area or approximately 100 sweat glands. Now, consider some sweat generation rates provided from the book: 'Dermatology: an illustrated color text" 5th edition. The human body excretes a minimum of 0.5 liter per day of sweat, and has 2 5 million sweat glands on average and there are 1440 minutes per day. For prepubescent children, these values for total sweat or sweat generation rate are typically lower. For 2.5 million glands that is rate of 0.2 μl per gland per day or 0.14 nl/min/gland. This is the minimum 'average' sweat generation rate, on average, with some possible exceptions being where sweating increases slightly on its own (such as measuring sleep cycles, etc.). Again, from 'Dermatology: an illustrated color text" 5th edition, the maximum sweat generated per person per day is 10 liters which on average is 4 μL per gland maximum per day, or about 3 nL/min/gland. This is about 20× higher than the minimum sweat generation rate.

The maximum stimulated sweat generation rate according to Buono 1992, J. Derm. Sci. 4, 33-37, "Cholinergic sensitivity of the eccrine sweat gland in trained and untrained men", the maximum sweat generation rate by pilocarpine stimulation are about 4 nL/min/gland for untrained men and 8 nL/min/gland for trained (exercising often) men. Other sources indicate maximum sweat generation rates of an adult can be up to 2-4 liters per hour or 10-14 liters per day (10-15 g/min·$m^2$), which based on the per hour number translates to 20 nL/min/gland or 3 nL/min/gland. Sweat stimulation data from "Pharmacologic responsiveness of isolated single eccrine sweat glands" by K. Sato and F. Sato (the data was for extracted and isolated monkey sweat glands, which are very similar to human ones) suggests a sweat generation rate up to about 5 nL/min/gland is possible with stimulation, and several types of sweat stimulating substances are disclosed. For simplicity, we can assume for use in calculations in the present invention (but not so limit the present invention) that the minimum sweat generation rate on average is about 0.1 nL/min/gland and the maximum sweat generation rate is about 5 nL/min/gland, which is about a 50× difference between the two.

Based on the assumption of a sweat gland density of 100/cm$^2$, a sensor that is 0.55 cm in radius (1.1 cm in diameter) would cover about 1 cm$^2$ area or approximately 100 sweat glands. Next, assume a sweat volume under a skin-facing sensor (space between the sensor and the skin) of 50 μm average height or 50×10$^{-4}$ cm, and that same 1 cm$^2$ area, which provides a sweat volume of 50E-4 cm$^3$ or about 50E-4 mL or 5 μL of volume. With the maximum sweat generation rate of 5 nL/min/gland and 100 glands, it would require a 10 minutes to fully refresh the sweat volume (using 1$^{st}$ principles/simplest calculation only). With the minimum sweat generation rate of 0.1 nL/min/gland and 100 glands, it would require 500 minutes or 8 hours to fully refresh the sweat volume. If the sweat volume could be reduced by 10× to a volume height of 5 μm roughly, the max and min times would be 1 minute and 1 hour, respectively, but the min time would also be subject to diffusion and other contamination issues (and 5 um dead volume height would be technically challenging). Times and rates are inversely proportional (rates having at least partial units of 1/seconds), therefore a short time required to refill the sweat volume can also be said to have a fast or high sweat sampling rate.

The space between the sensor and the skin could be a microfluidic component. For example, a 25 μm thick piece of paper or glass fiber covering an area of 1 cm$^2$ would equate to a volume of 2.5 μL; if the paper was 50% porous (50% solids), then the sweat volume would be 1.25 μL. With the maximum sweat generation rate of 5 nL/min/gland and 100 glands, it would require 2.5 minutes to fully refresh the sweat volume. With the minimum sweat generation rate of 0.1 nL/min/gland and 100 glands it would require about 100 minutes to fully refresh the sweat volume. "Fully refreshing" is a term that in some cases should be interpreted loosely unless further details or calculations are provided. Because of mixing and diffusion over time, the moment of having a "fresh sweat volume" must be determined using finer details of the specific usage and device and situation in question.

The above examples could in some cases be interpreted to provide a sampling interval for sweat, that is the sampling interval would be roughly how long it would require for sweat to fill, or refill, space, in some cases a space where significant diffusion, mixing, and contamination could occur. A sampling interval for sweat could also be more broadly interpreted to include the actual transport, diffusion, or contamination times of those aspects of sweat that are to be measured. Sampling intervals could vary widely. For example, because small ions may diffuse much more readily than large proteins, both could be measured solutes that are affecting the sampling interval. Sampling intervals could vary widely, for example, based on finer aspects of device design, such as designs where sweat is always flowing forward from skin to sensors and beyond vs. devices where the somewhere between the sensors and the skin there are one or more dead or stagnant volumes of sweat. Therefore, the term sampling interval should be interpreted broadly and in some cases will need to be determined experimentally on a case-by-case basis for each aspect of sweat that is to be measured.

Sweat stimulation, or sweat activation, can be achieved by known methods. For example, sweat stimulation can be achieved by simple thermal stimulation, by orally administering a drug, by intradermal injection of drugs such as methylcholine or pilocarpine, and by dermal introduction of such drugs using iontophoresis. A device for iontophoresis may, for example, provide DC current and use large lead electrodes lined with porous material, where the positive pole is dampened with 2% pilocarpine hydrochloride and the negative one with 0.9% NaCl solution. Sweat can also be controlled or created by asking the subject using the patch to enact or increase activities or conditions which cause them to sweat. These techniques may be referred to as active control of sweat generation rate.

Traditionally, sweat generation rate can be measured by fairly crude methods that do not provide real time continuous monitoring of sweat generation rate. In order to visualize sweat glands, two methods have been used, i.e., the starch-iodine test and a method that allows permanent recording of sweat drops in silicone. The latter method consists of stimulating sweat production, drying out the skin, and then applying a thin layer of liquid silicone to it. Prior to utilization, the silicone is mixed with a catalyzer that polymerizes and solidifies the material in about 90 seconds. The solid silicone is then manually removed, and sweat drops are counted and measured by prints left on the material. Another method involves collecting sweat biomarker content such as sodium concentration that increases with sweat generation rate, and measuring it using bench top equipment. These example techniques for measuring sweat generation rate are useful in some cases for pre-determining sweat generation rate for an individual or specific situation. Values from literature that map out sweat generation rates for various persons, ages, body locations, activity levels, etc. and manually couple them with other variables that will affect sweat generate rates (e.g. activity level and room temperature) may be used to predetermine sweat generation rate. Such sweat generation rates could be built into a sweat sensing system, or they may be programmed as needed into such a system. These techniques can be referred to as predetermined sweat generation rate.

Sweat generation rate can also be measured real time in several ways. Both sodium and chloride, which are excreted by the sweat gland during sweating, can be utilized to measure sweat generation rate in real time (higher sweat generation rate, higher concentration). Both sodium and chloride can be measured using ion-selective electrodes or sealed reference electrodes, for example placed in the sweat sensor itself and measured real time as sweat emerges onto the skin. Sato 1989, pg. 551 provides details on sweat generation rate vs. concentration of sodium & chloride. Electrical impedance can also be utilized to measure sweat generation rate. Grimnes 2011 and Tronstad 2013 demonstrate skin electrical impedance and sweat generation rate correlations. Impedance, sodium concentration, and/or other measurements can be made and used to determine at least roughly the sweat pore density and sweat generation rate from individual sweat glands, and, when coupled with sweat sensing or collection area, can be used to determine an overall sweat generation rate to a sensor. Common electronic measurements to also predict sweat generation rate include those such as pulse, pulse-oxygenation, respiration, heart rate variability, mental activity, overall body activity level, and 3-axis accelerometry, or other common readings published by Fitbit, Nike Fuel, Zephyr Technology, and others in the current wearables field. These techniques can be referred to as measured sweat generation rate. Techniques for measured sweat rate can also be used before use of a sweat measuring device to obtain predetermined sweat generation rates for use with the sweat measuring device.

The present invention applies at least to any type of sweat sensor device that measures sweat, sweat generation rate, sweat chronological assurance, its solutes, solutes that transfer into sweat from skin, a property of or things on the surface of skin, or properties or things beneath the skin. The present invention applies to sweat sensing devices which can take on forms including patches, bands, straps, portions of clothing, wearables, or any suitable mechanism that reliably brings sweat stimulating, sweat collecting, and/or sweat sensing technology into intimate proximity with sweat as it is generated. Some embodiments of the present invention utilize adhesives to hold the device near the skin, but devices could also be held by other mechanisms that hold the device secure against the skin, such as a strap or embedding in a helmet.

Certain embodiments of the present invention show sensors as simple individual elements. It is understood that many sensors require two or more electrodes, reference electrodes, or additional supporting technology or features which are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a sweat sensor; an impedance sensor; a sweat volume sensor; a sweat generation rate sensor; and a solute generation rate sensor. Certain embodiments of the present invention show sub-components of what would be sweat sensing devices with more sub-components needed for use of the device in various applications, which are obvious (such as a battery), and for purpose of brevity and focus on inventive aspects are not explicitly shown in the diagrams or described in the embodiments of the present invention.

With reference to FIG. 1, a sweat sensor device 100 is placed on or near skin 12. In an alternate embodiment, the sweat sensor device may be simply fluidically connected to skin or regions near skin through microfluidics or other suitable techniques. Device 100 is in wired communication 152 or wireless communication 154 with a reader device 150. In one embodiment of the present invention, reader device 150 would be a smart phone or portable electronic device. In alternate embodiments, device 100 and reader device 150 can be combined. In further alternate embodiments, communication 152 or 154 is not constant and could be a simple one time data download from device 100 once it has completed its measurements of sweat.

Figure 2:
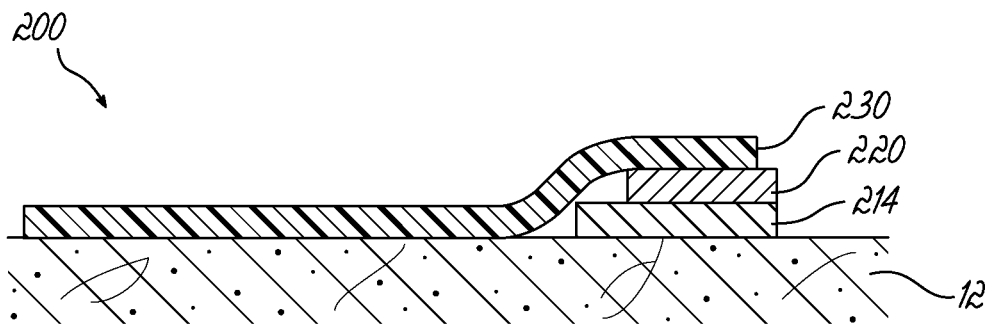
FIG. 2 is an elevation view of at least a portion of an example embodiment of the present invention illustrating a predetermined sweat volume determined from the volume between the sweat sampling site on the skin and the sensor and a predetermined sweat generation rate.

With reference to FIG. 2, microfluidic component 230 carries sweat from skin 12 to sensor 220 that is placed on impermeable substrate 214. For example, sensor 220 can be an impedance sensor for a cytokine biomarker, and impermeable substrate 214 can be a polyimide film. Sensor 220 measures one or more solutes in sweat or the presence or flow rate of sweat. In device 200, microfluidic component 230 could have a predetermined sweat volume between sensor 220 and skin 12 that is determined at the time of manufacturing. Microfluidic component 230 could be, for example, paper, a polymer microchannel, a tube, or a gel, or other means to transport sweat from skin 12 or more directly from sweat ducts themselves to sensor 220. If the volume of microfluidic component 230 is small, then the sweat flow rate will be higher across the sensor 220 and will mitigate diffusion of contaminating solutes or mixing of fluids collected at previous times. A better chronological assurance is provided by reducing back diffusion of solutes from previously generated sweat that has wicked beyond sensor 220. For continuous monitoring, microfluidic component 230 could wick sweat past the sensor 220 to a hydrogel that continuously absorbs, which therefore pumps sweat from skin 12 and across sensor 220 at the rate at which sweat is provided from the skin.

For an example of device 200 in use, the device could be used with a runner during a race with the runner having a predetermined sweat generation rate of 5 nL/min/gland during the race, determined by previously measuring sweat generation rate in a controlled/artificial situation for the runner. The microfluidic component could be a 25 µm thick piece of paper or glass fiber covering 100 glands, or 1 cm$^2$, equating to a sweat volume of 2.5 µL ($25\times10^{-4}$ cm$\times$1 cm$\times$1 cm=$25\times10^{-4}$ cm$^3$=$2.5\times10^{-3}$ mL). If the paper was 50% porous (50% solids), then the predetermined sweat volume would be 1.25 µL. Therefore, the sweat sampling rate, for example, could be calculated as 1.25 µL/(5 nL/min/gland$\times$100 glands)=2.5 min Therefore, sweat sensing device 200 could provide a chronological assurance of 2.5 minutes, meaning that the data the device reports could be interpreted to represent at least one physiological measurement of the runner that is determined from newly generated sweat within a window of time of approximately 2.5 minutes. This is a first order type calculation, which in some cases could be highly accurate for looking at, for example, the onset of a significant increase of a particular solute in sweat.

In alternate embodiments of the present invention, the chronological assurance may need to be corrected for confounding factors such as contamination by back diffusion or from skin or other sources of contamination. This assumes that a measurement of sweat or skin is immediately relative to what is happening inside the body, which in some measurements is highly accurate (e.g. sweat gland activity and a sodium concentration in sweat generated immediately by the sweat gland), but may be less accurate in others (e.g. a cytokine biomarker indicating increasing inflammation and injury, which slowly builds up in the body and passively diffuses into sweat). For particular biomarkers of interest, the chronological assurance can be informed by additional known medical knowledge of relation to measurements outside the body to what is happening inside the body.

Figure 3:
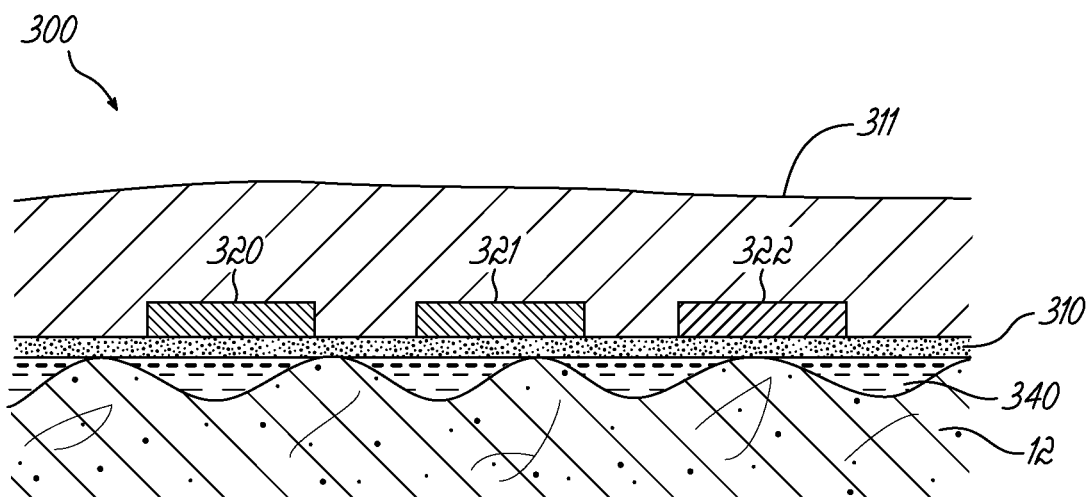
FIG. 3 is an elevation view of at least a portion of an example embodiment of the present invention illustrating a predetermined sweat volume determined from a volume between the skin and the sensor and a sweat generation rate determined through the measurement of at least one biomarker and a measurement of the electrical impedance of the skin.

With reference to FIG. 3, device 300 includes material 311 that carries two or more sensors, 320 and 321, and reference electrode 322, and has below it adhesive 310 and volume 340 between these features and skin 12. For example, adhesives can be pressure sensitive, liquid, tacky hydrogels, which promote robust electrical, fluidic, and iontophoretic contact with skin. Material 311 could be, for example, porous to sweat, wick sweat like a hydrogel or textile, or be impermeable to sweat. Skin 12 has a roughness to it, which is illustrated in FIG. 3. Even with adhesive 310, in some embodiments of the present invention, volume 340 would exist, which in combination with the available porous volume or sweat uptake volume of adhesive 310 could provide a predetermined sweat volume between skin 12 and sensors 320, 321, and 322. In an alternate embodiment of the present invention, volume 340 could also be gel or adhesive, separate or combined with adhesive 310, such that their volume and open porosity to sweat, or ability to swell and absorb sweat, could be utilized to calculate volume between sensors 320, 321, and 322 and skin 12 in a predetermined way. Adhesive 310 may also be flexible or deformable enough that it dominantly or fully occupies the volume 340. For example, sensor 320 could be an ion-selective electrode to measure sodium, sensor 321 could be an electrical impedance spectroscopy sensor to measure IL-6, and sensor 322 could be a drift-free Ag/AgCl reference electrode. Sweat generation rate could be measured by sodium concentration by sensor 320, and sweat generation rate could also be measured by impedance by sensor 321, providing together a measured sweat generation rate. Reference electrode 322 should preferably be centimeters or more away from sensor 321 if the most accurate impedance measurement into the skin is to be measured.

For an example of device 300 in use, device 300 could be adhered to a skin location that was smoothed or that inherently has a depth of grooves limited to 10 µm (averaged height of volume 340 would be 5 µm). If sensor 320 had an area of 10 mm$^2$, and the volume of adhesive 310 was negligible, the predetermined sweat volume would be at least 50 nL. From a calibrated look-up table for sweat pore density based on placement location on the body, an average of 10 pores under the sensor 320 would be determined. If the sweat generation rate was 0.1 nL/min/gland, the effective sweat flow rate would be 1 nL/min, and the sweat sampling interval would therefore be 50 minutes. Because this is a relatively slow sampling interval, effects of diffusion and other contamination may need to be incorporated for some types of measurements. Therefore, this device 300 could alert the user that the chronological assurance is likely undeterminable with the limited inputs it has because of the diffusion of contaminants. If the sweat generation rate increased to 1 nL/min/gland, the chronological resolution would drop to 5 minutes, at which the point the device could provide information that the chronological assurance is 5 minutes and can likely be trusted.

Skin wrinkles can be tens of microns in depth, with a roughness that can be greater than 10 µm. The skin or device can deform, swell, or change in physical geometry. Some skin, as it becomes moist, swells and reduces sweat flow rate (especially finger tips and feet where skin is thick). All of this information can be used to inform in predetermined or measured ways the sweat volume, sweat generation rate, sweat sampling rate, and therefore the chronological assurance.

Determining the sweat generation rate may require multiple measurements or determinations. For example, the number or density of sweat pores in some embodiments of the present invention needs to determined. Because electrical impedance, sodium, or other solute concentration in sweat can be determined by the sweat generation rate per gland, in some cases the number of glands that sweat is being collected from needs to be known so that the overall flow rate of sweat can be used to better understand measurements of sweat. Furthermore, if sweat generation rate per gland is determined by, for example, sodium concentration, then the number of glands could be determined to then further determine the rate of flow of sweat through device 300. The number of glands could be predetermined or measured. If the sweat sampling area is measured or predetermined, and the number of sweat glands are measured or predetermined, the sweat sampling area and number of sweat glands can be used to determine the density of sweat glands per unit area or vice-versa. The number or density of sweat glands could be predetermined by data entry of the location of device 300 placement on the body, the user's age, and a lookup table of sweat gland densities and their maximum sweat generation rates on the body as a function of age. The number or density of sweat glands could also be measured. For example, measuring impedance would in some cases be dominated by the low impedance of the sweat gland during active sweating, if the impedance of the skin was measured without or at low sweating, then the difference between the two could be used to determine the number or density of sweat glands. Furthermore, if the collection area, sweat flow rate per gland, and flow rate are predetermined or measured, then the number or density of sweat glands can be determined. Flow rate measurement techniques known in the art of microfluidics, including thermal flow sensors and microelectromechanical flow sensors, can be integrated with one or more microfluidic components or at other locations or features of the present invention.

Figure 4:
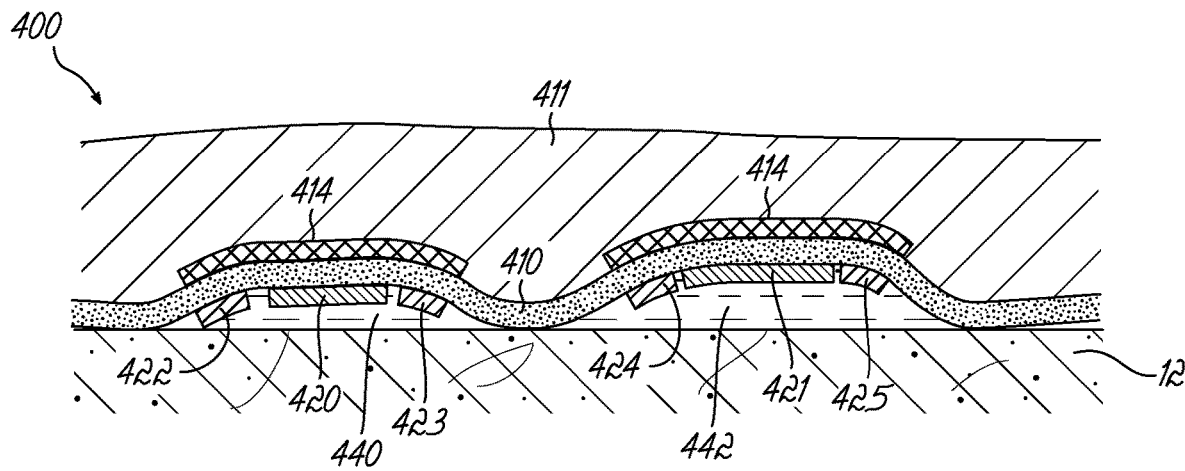
FIG. 4 is an elevation view of at least a portion of an example embodiment of the present invention illustrating a sweat generation rate determined by a measurement of impedance and a plurality of sweat volumes between the sweat sampling site on the skin and the sensor determined through a measurement of impedance, where two or more sensors are individually equipped to provide chronological assurance.

The effective sweat sampling rate, and therefore chronological assurance, can be determined by both determined sweat generation rate and determined sweat volume. Sweat volumes or portions of sweat volumes could be measured by a variety of techniques, such as electrical methods, as absorption spectroscopy, mechanical waves, and other techniques. FIG. 4 illustrates an embodiment of the present invention where sweat volumes are measured using simple electrical sensing. With reference to FIG. 4, device 400 includes sensors 420 and 421, which have two different sweat volumes, 440 and 442, between said sensors and skin 12. Note that chronological assurance can be provided individually for subcomponents or sub-sensors of a device. Sweat volumes 440 and 442 could be simply variations in spacing between sensors 420 and 421 and skin 12 since adhesive 410 is on the side of sensors 420 and 421 away from skin 12. In addition to carrying features similar to FIG. 3, device 400 also includes electrode pairs 422 and 423, and electrode pairs 424 and 425 for the purpose of measuring sweat volumes 440 and 442. Sensors 420 and 421, electrode pairs 422 and 423, and electrode pairs 424 and 425 are supported by a substrate 414. Substrate 414 may be, for example, impermeable to sweat and electrically insulating. Hydrogel or wicking textile 411 may capture excess sweat as it is generated. Electrode pairs 422 and 423 and electrode pairs 424 and 425 measure primarily electrical impedance (primarily resistance) of the sweat between their adjacent sensor, 420 or 421, and skin 12. If sensors 420 and 421 were suitably electrically insulated from sweat, such as coated ion-selective electrodes, the electrode pairs may better measure impedance. Alternately, impedance could be measured between at least one of conductive sensors 420 and 421 and an adjacent electrode such as 422, 423, 424, or 425. The top layer of skin 12 is typically fairly electrically insulating compared to sweat, and therefore the impedance measured can be used to calculate the sweat volume beneath each sensor 420 and 421 by electrical impedance of the sweat. However, a simple measurement of volume by electrical resistivity will also be dependent on ion concentration, especially sodium and chloride, both of which change with sweat generation rate. Therefore, sensors 420 and 421, or possibly another sensor added (not shown) near sensors 420 and 421, can measure ion content such as sodium or chloride and use that to calculate the electrical conductivity of the sweat, which is in turn used along with the impedance measurements from electrode pairs 422 and 423 and electrode pairs 424 and 425 to provide a more accurate determination of sweat volumes 440 and 442 by measured impedance. Ion concentrations, such as concentrations of sodium and chloride, could also be measured by interpretation of measurement of sweat generation rate using one or more methods to measure sweat generation rate. Either sensor 420 or 421 could be used to measure sodium or chloride and therefore predict sweat generation rate. Sweat generation rate can be measured using impedance measurement sensors, for example, using additional electrodes, or potentially even one or more of electrodes or sensors 420, 421, 422, 423, 424, and 425.

Sweat volumes 440 and 442 could vary significantly due to variation in heights of micrometers to millimeters, adhesion variation, patch placement, scars, moles, wrinkles or grooves on the skin (impedances of a groove(s) filled with sweat could be measured if that is the only sweat volume), particulates or dust, or hair. Even with proper preparation of the skin, a shaved hair may grow enough during several hours of monitoring to alter volume 440 or 442. In some cases, a gel or soft material could be added to help fill in such volumes and reduce sweat volume, but many such materials will slow the transport of solutes in sweat to the sensors. Furthermore, in areas where such a gel or soft materials is not needed, it could increase the sweat volume if such material is thick and porous.

Figure 5:
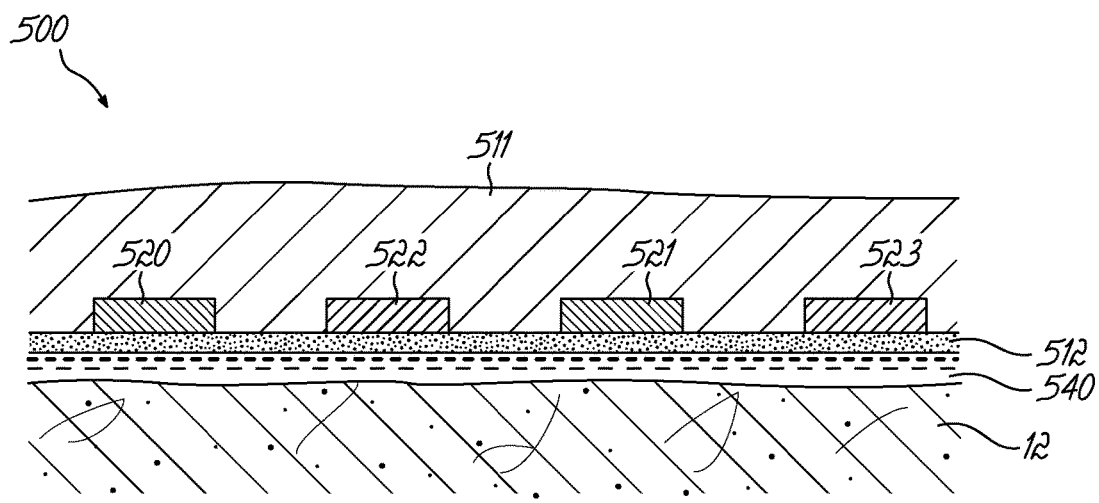
FIG. 5 is an elevation view of at least a portion of an example embodiment of the present invention illustrating a determination of one or more sweat volumes between the sweat sampling site on the skin and the sensors by at least one measurement of impedance and a sweat generation rate determined through a measurement of impedance.

With reference to FIG. 5, device 500 includes membrane 512 that isolates sensors 520 and 521 and/or electrodes 522 and 523 from direct contact with skin 12, which prevents fouling of surfaces of sensors 520 and 521 or electrodes 522 and 523 but allows transport of fluid such as water and solutes to be sensed. For example, membrane 512 could be a thin dialysis membrane. Electrodes 522 and 523 can vertically measure the gap and volume 540 using impedance. In an exemplary embodiment, electrodes 522 and 523 would measure the gap and volume 540 when the gap or volume 540 is in a state significantly void of sweat, such that gap or volume 540 has the highest electrical impedance of the vertical measurement of impedance down into skin 12. This can be performed, for example, when the patch is first applied (before sweating), at intervals when sweat ceases due to inactivity of the test subject, or at intervals when sweat stimulation ceases such that sweat is wicked away by gel or wicking material 511 and gap or volume 540 is made suitably dry. The gap and volume 540 could be further measured when it is significantly filled with sweat, such that the difference of impedance between the states of being significantly void vs. significantly filled could provide an improved determination of volume 540. Electrodes 522 and 523 could also measure sweat generation rate by impedance, and therefore chronological assurance be provided dominantly through measured means.

Figure 6:
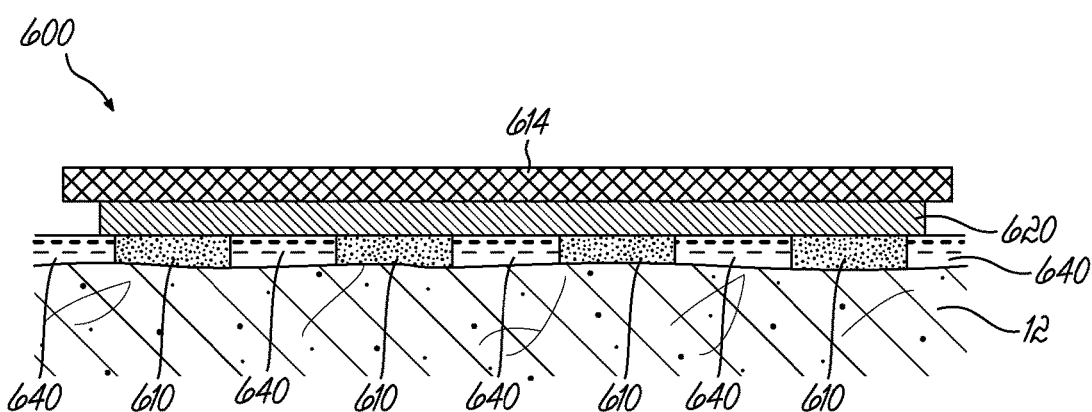
FIG. 6 is an elevation view of at least a portion of an example embodiment of the present invention illustrating a predetermined sweat volume between the sweat sampling site on the skin and the sensors and a sweat generation rate determined by a sensor which also measures another property of sweat itself.

FIG. 6 illustrates an example embodiment of the present invention where device 600 includes a predetermined sweat volume 640 between the sweat sampling site on skin 12 and sensor 620 and a sweat generation rate determined by sensor 620 measuring impedance. Sensor 620 could be, for example, an electrode functionalized with gold nano-particles, which create a very high surface area for the electrode comprising sensor 620. The gold nanoparticles can be functionalized with an aptamer specific to a cytokine such as IL-6 where the combination of the high surface area of the electrode comprising IL-6 and the thin nature of the surface functionalization provide an impedance low enough such that sensor 620 can also be used to determine sweat generation rate by impedance. Adhesive 610 may be patterned with a specific height such that sweat volume 640 is largely predetermined by the height of adhesive 610. The sweat, as it emerges from skin, must flow around sensor 620 and sweat impermeable substrate 614. The sweat sampling interval may be determined using a microfluidic model or algorithm that accounts for the fact that sweat emerging near the center of sensor 620 will take longer to clear from beneath sensor 620 than sweat emerging from near the edges of sensor 620. Therefore, the chronological assurance is calculated from a sweat sampling interval that is partly measured and partly predetermined.

Figure 7:
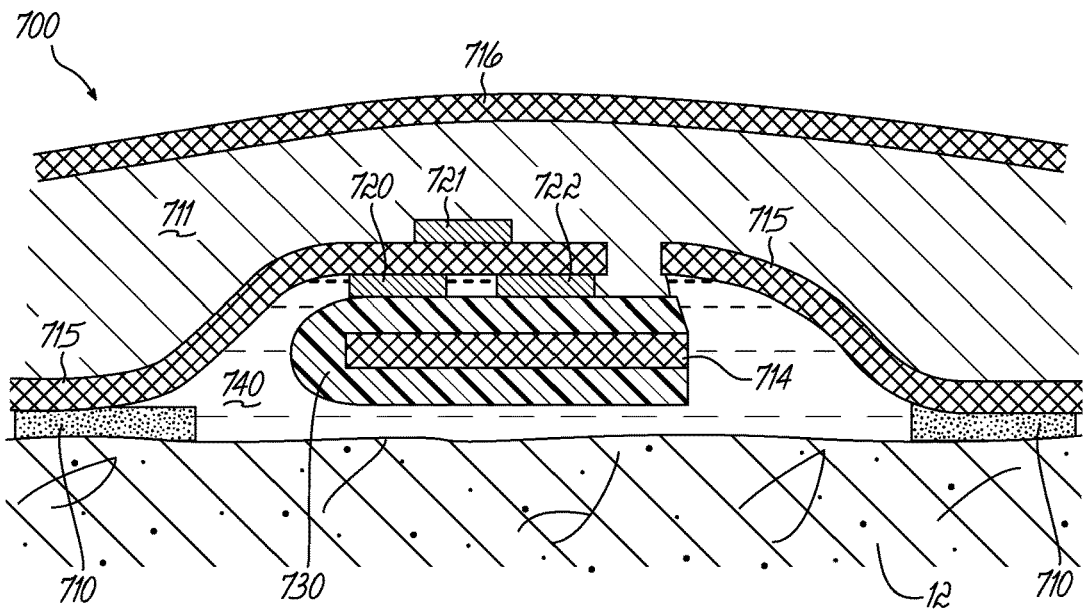
FIG. 7 is an elevation view of at least a portion of an example embodiment of the present invention illustrating determined sweat volumes between the sweat sampling site on the skin and the sensors, a sweat generation rate determined through a measurement of a sweat biomarker, and a sensor that measures concentration of solutes which could alter transport of solutes in sweat or measure rate at which solutes can diffuse back to the sensing location for such solutes.

With reference to FIG. 7, device 700 contains an absorbing gel or material 711, adhesive 710, and impermeable substrates 716, 715, and 714. Impermeable substrate 716 could also be fluid resistant but vapor porous to allow evaporation of collected sweat. When adequate sweat is generated by skin 12 to make contact with microfluidic component 730, sweat is wicked past sensor 720 to gel or wicking material 711. Electrode or sensor 722 is able to determine sweat generation rate by measuring impedance through microfluidic component 730 and substrate 714. Electrode or sensor 722 may also be able to determine sweat generation rate through measuring lower frequency impedance along a sweat saturated microfluidic component 730 into skin 12 when volume 740 is also substantially filled with sweat. Sensor 722 could measure volume 740 using similar means described for FIG. 5. Device 700 is also equipped with sensor 721, which can measure a concentration solute of sweat inside gel or absorbing material 711 or a concentration solute of sweat relative to concentration of that same solute at sensor 720. From this, the amount of back-diffusion or other mechanism of transport of that solute towards the skin can be calculated using the laws of diffusion and microfluidics or determined experimentally and found by a look-up table for device 700. In this way, sweat sampling rate and chronological assurance are informed by more than just advective transport of fluids and include a measure of contamination of the sweat sampling rate by previously collected solutes. Sensor 721 or additional sensors not shown could be used to also measure how full or hydrated the gel or absorbing material 711 is, which could affect the rate of wicking of sweat from skin 12 past sensor 720. When fully hydrated or full, the gel or absorbing material 711 could cause flow to stop completely across sensor 720, and the chronological assurance would be informed that it is very poor. In this way, sweat sampling rate, and therefore chronological assurance, is further informed more than just by sweat generation rate at the skin but also by advective transport rates through the device past the sensors.

Figure 8:
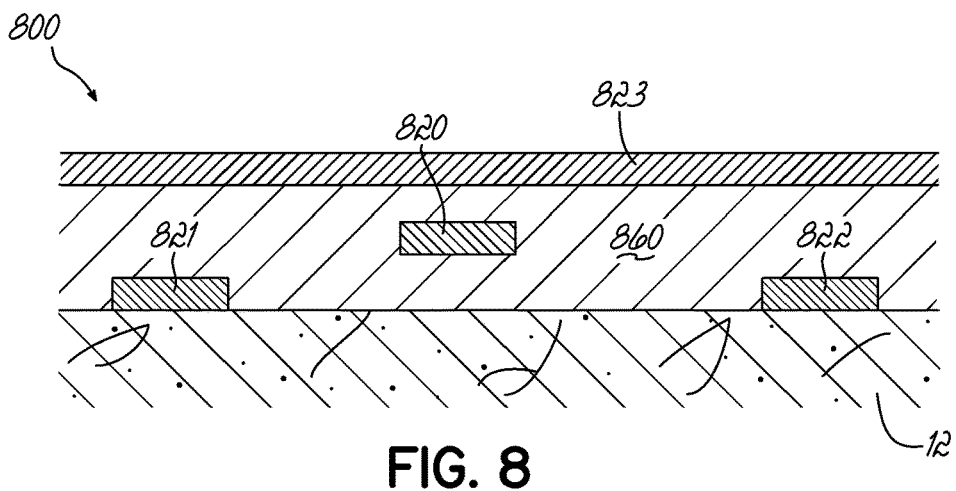
FIG. 8 is an elevation view of at least a portion of an example embodiment of the present invention illustrating measurement interference of iontophoresis or diffusion on chronological assurance.

With reference to FIG. 8, device 800 includes an iontophoresis electrode 823, a gel or porous matrix with pilocarpine 860, sensor 820, and impedance sensors 821 and 822 used to determine sweat generation rate. Electrode 823 could be, for example, porous such as carbon paper or other iontophoresis compatible material coated on a porous surface, such that sweat can evaporate from device 800 or be transported to a collection or absorbing component like that shown in other embodiments of the present invention. The impedance could be used to determine sweat generation rate real time. Gel 860 could have a known diffusivity for solutes in sweat. Some solutes or sweat from previously generated solutes or sweat could diffuse into and out of gel 860 over time and result in chronological contamination of newly generated sweat or its solutes. This can be referred to as a predetermined solute transport, which can be used to further determine the chronological assurance. One or more of electrodes 821 and 822 could be used to measure iontophoretic transport of ions through gel 860 and/or the electrical conductivity of gel 860. Therefore, back-calculating an estimate of diffusion or ease of solute transport through gel 860 would provide a measured solute transport. Furthermore, if the solutes to be sensed by sensor 820 are ionic in nature, the electric field (either continuous or non-continuous) provided by iontophoresis electrode 823 could interfere with transport of ionic solutes from sweat or skin 12 to sensor 820. Such interference could be quantified using one or more electrodes 821, 823, and 822, potentially by sensing the ionic solute while the electric field or current is applied between any of electrodes 821, 823, and 822. Furthermore, the porosity or solute transport rate of solutes in sweat from skin 12 to sensor 820 of gel 860 could be low and slow, which would reduce the chronological resolution, and could be measured or calculated in a predetermined manner to therefore further determine the chronological assurance. As illustrated, the effects of diffusion, electrophoresis, or even electroosmosis on chronological assurance for device 800 can be measured or predetermined.

Figure 9:
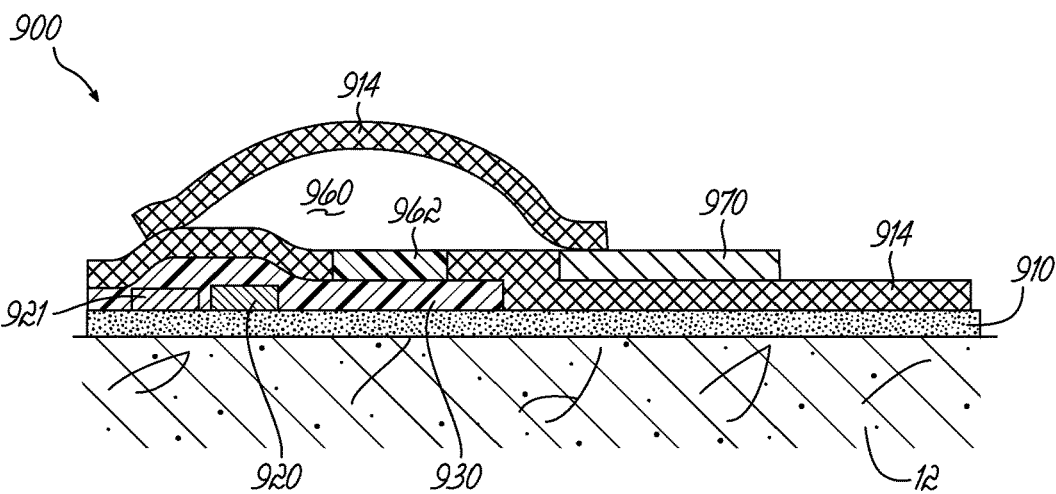
FIG. 9 is an elevation view of at least a portion of an example embodiment of the present invention illustrating active control of a sweat generation rate by introduction of a sweat stimulant and by measurement of sweat generation rate by impedance to inform the active control of chronological assurance through feedback control.

With reference to FIG. 9, device 900 includes adhesive 910, substrate 914, sensor 920, electrode 921, microfluidic component 930, reservoir 960, microfluidic gate 962, and electronics 970. Reservoir 960, which is sealed, contains a solution of sweat stimulant such as pilocarpine, methacholine, or other stimulants, especially smaller molecule stimulants, and their known solvents such as water, alcohols, etc. and pH adjusters as needed. Reservoir 960 contains microfluidic gate 962, which can controllably introduce sweat stimulant to microfluidic component 930. The sweat stimulant can be utilized to stimulate sweat by iontophoresis using two or more electrodes, such as electrode 921 and a counter electrode elsewhere (not shown), or by passive diffusion, albeit likely with a lower stimulated sweat generation rate if diffusion is used. Electrical control of sweat stimulation could therefore be controlled by iontophoretic current from electrodes such as electrode 921, and/or by control of microfluidic gate 962. Microfluidic gate 962 can be any means suitable to introduce sweat stimulant in a controlled manner, for example, including thermocappilary, electrowetting, voltage regulated ion-channels (by ion accumulation or depletion in channels), electrophoresis, or other mechanisms known in the art of microfluidics.

With further reference to FIG. 9, device 900 also includes electronics 970, which can receive information such as sweat generation rate or sweat flow rate in device 900 from a sensor sensing sweat generation rate through a biomarker (such as sensor 920), a sensor sensing sweat generation rate through impedance (such as electrode 921), or any other suitable mechanism to determine or inform sweat generation rate or sweat flow rate including those external to the patch (such as external environmental temperature or body motion and exertion as measured by device 900 or an external communicating device such as smart phone or other wearable device). Based on determination of a sweat generation rate, sweat stimulation rate can then be controlled by the electronics 970 as well. Therefore, chronological assurance can be actively controlled by a feedback control mechanism (e.g. if sampling interval is too long, sweat stimulation is increased). This active control of sweat generation rate and sweat sampling rate, and therefore of chronological assurance, can be static for a given device 900 (determined at the time of manufacture or programming before device 900 is sold or used), or adjusted in real time based on user inputs or biomarker readings from the body from device 900 or other biosensor devices beyond device 900.

Any combination of pre-determined or measured sweat flow rate, sweat volume, and therefore sampling interval and chronological assurance can be utilized to provide active control of chronological assurance. For example, the sweat flow rate and the sweat volume could both be predetermined, which means chronological assurance can be provided for a given sweat flow rate. The device can simply influence sweat generation rate by active control of stimulation and therefore is able to inform changes in chronological assurance based on the control of stimulation alone.

With further reference to FIG. 9, electronics 970 or other subcomponents shown for the present invention could also be external to device 900, for example contained in a smart phone. Electronics may of course include computing and algorithms, or other aspects needed for proper function. As an example of active control of chronological assurance using device 900 where electronics 970 are contained in a smart phone, the electronics may prompt the smart phone to alert the user of the device 900 that chronological assurance has decreased to a low level and the user should take an orally administered sweat stimulant or increase their activity level to maintain the chronological assurance.

The feedback control and therefore active control of chronological assurance illustrated by FIG. 9 may of course apply to any other embodiments of the present invention where sweat generation rate is stimulated or actively controlled in any manner Alternate embodiments of the present invention include alternate embodiments as taught in U.S. Provisional Applications Nos. 61/892,859 and 62/003,707. The present invention can provide not only active chronological assurance for a device, but also individually for subcomponents or sub-sensors of a device, for example, some biomarkers in sweat may need to be measured only every several hours, because they change slowly in the body, where some need to be measured every few minutes. Chronological assurance and/or active control or feedback control may therefore be different for the subcomponents of a device. For example, sweat stimulation could be integrated with the plurality of sensors shown and described in the embodiment of FIG. 4, where each sensor could have localized active control of sweat stimulation and where the stimulation could occur at regular or irregular intervals, as needed, based on feedback control or external inputs. For example, sensors could sense biomarkers of the effects and extent of tissue damage at a slower sweat sampling rate than sensors that could sense biomarkers of short term stress or trauma on the body, the trauma sensors having locally higher sweat stimulation than the tissue damage sensors.

In an alternate embodiment of the present invention, sweat stimulation may be auto-regulated by sweat generation rate. Either passive diffusion or iontophoresis is utilized to deliver a sweat stimulant such as pilocarpine, but the rate of delivery is controlled in part by the flow of sweat out of the gland which is in the opposite direction of the sweat stimulant delivery. In an advanced form, the sweat generation rate would be controlled at a fairly steady level by providing a pre-determined concentration of pilocarpine exposed to the skin, possibly even by changing that concentration of pilocarpine exposed to the skin by electrical or microfluidic transport between a reservoir of pilocarpine and the skin. In this case, the sweat generation rate and chronological assurance could be inherently controlled without electronics, and chronological assurance simply needs to be measured and informed using one or more principles of the present invention. However, in some cases this may require that the difference between concentration at the skin surface and the target sites in skin for stimulation of sweat be regulated in some manner as diffusion is dependent on concentration gradient. The sweat generation rate would increase as sweat stimulant concentration is increased during or before use of the device.

Sweat generation rate could also be actively controlled by other methods. For example, sweat generation rate may be made to decrease by iontophoresis of a drug which reduces sweating, such as anticholingerics including glycopyrrolate, oxybutynin, benztropine, and propantheline. Sweat generation rate could also be reduced by administering a solvent to the skin such as glycols which can swell the top layer of skin and pinch off the sweat ducts resulting in constriction of flow of sweat to the surface of skin. Other antiperspirant compounds such as Aluminum chloride may be used as well. Why would one want to slow the sweat generation rate since in most cases that would reduce chronological assurance? Two non-limiting examples include the following. Firstly, some sensors or subcomponents could foul or degrade in performance more quickly as fresh sweat is brought to them, or the general maximum usage time of the patch may decrease as a result of a sweat generation rate that is too high. The sweat sampling rate could be reduced for a patch by using a gate, such as a gate like gate 962, between the skin and the sensor or microfluidic component to control the introduction of sweat to a sensor or microfluidic component. Second, some solutes or properties of sweat could be read more reliably at lower sweat generation rates. In particular, low concentration solutes could have more time to diffuse into slowly flowing sweat inside the sweat gland/duct, and therefore a lower sweat generation rate could produce a higher concentration which could be more easily sensed by a sensor. Furthermore, some solutes are generated by the sweat gland itself during high levels of sweat generation (such as lactate) and could interfere with sensors for other solutes or sensors trying to sense lactate diffusing into sweat from blood.

Figure 10:
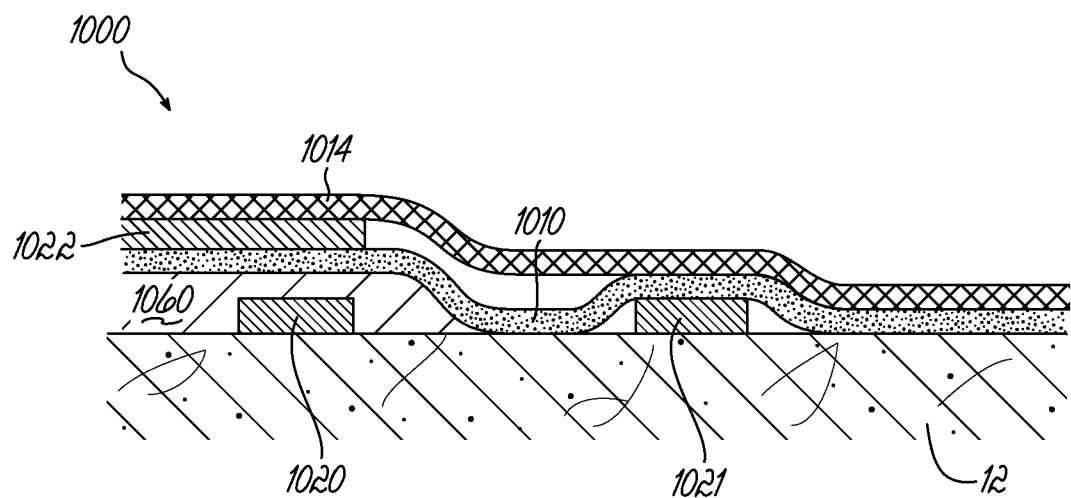
FIG. 10 is an elevation view of at least a portion of an example embodiment of the present invention illustrating at least one sensor to measure the interference of contaminants from skin.

With reference to FIG. 10, device 1000 includes sensor 1020, sensor 1021, iontophoresis electrode 1022, adhesive 1010, substrate 1014, and reservoir 1060, which could be filled with pilocarpine for example. Sensor 1021 could, for example, measure contamination coming from skin alone (as no sweat stimulation occurs near sensor 1021), which could inform chronological assurance for sensor 1020 in terms of biomarker contamination from skin vs. sweat. For example, glucose can diffuse through skin to the surface of skin 12 (slowly) and appears in sweat (more quickly) in representation of interstitial glucose or plasma glucose. The chronological assurance of sweat glucose could be informed by sensor 1021 since interference of skin diffusion glucose will represent in some cases a longer sampling interval compared to sweat glucose, thus altering the sweat sampling interval and chronological assurance. The measurement and chronological assurance could be improved as the signal from skin diffusing glucose (sensor 1021) could be subtracted from the signal from sweat glucose and skin glucose (sensor 1020) to provide only sweat glucose, thus further informing the chronological assurance of device 1000. It should be noted, that the present invention also includes measurements of solutes in sweat that diffuse into sweat from skin, and so the term 'contaminant' does not necessarily infer something that is not to be measured, nor is the skin excluded from measurement. Sensor 1020 could experience different skin transport rates of solutes compared to sensor 1021, because sensor 1020 could have electric field across its adjacent skin which would alter rate of appearance of solutes emerging from skin. Therefore, sensor 1021 could be equipped with electric field or solvents to mimic the environment around sensor 1020 for a more accurate chronological assurance.

With further reference to FIG. 10, electrode 1022 and its current or electric field could also be utilized to enhance (speed up) solute or biomarker extraction from skin into sweat or from sweat glands/ducts themselves, and therefore effectively reduce the sweat sampling interval which informs the chronological assurance. Iontophoresis and electroosmosis can therefore be included as alternate embodiments of active control of chronological assurance. Additional methods include electroporation or any other mechanism known to increase the rate of solute transport through fluids or biological membranes, or mechanisms which simply speed transport through components of device 1000. For example, electrophoresis can be utilized to increase the transport speed of solutes between skin 12, sweat glands in skin 12, and the sensors by applied electrical field and current, which may be of particular use where the component could be a microfluidic component. Therefore all embodiments where sweat generation rate is mentioned, solute generation rate can be used interchangeably to indicate cases where flow of actual sweat fluid may be fast, slow, or stagnant, but where solutes are actively (e.g. electric field) or passively (e.g. diffusing) at a faster or slower rate than the flow of the actual sweat fluid itself in the devices of the present invention. Sweat sampling rate may also therefore include and in part refer to solute sampling rate, and therefore be dependent on more than just sweat volume and sweat generation rate. Solute generation rate or solute sampling rate can be measured or predetermined.

Figure 11:
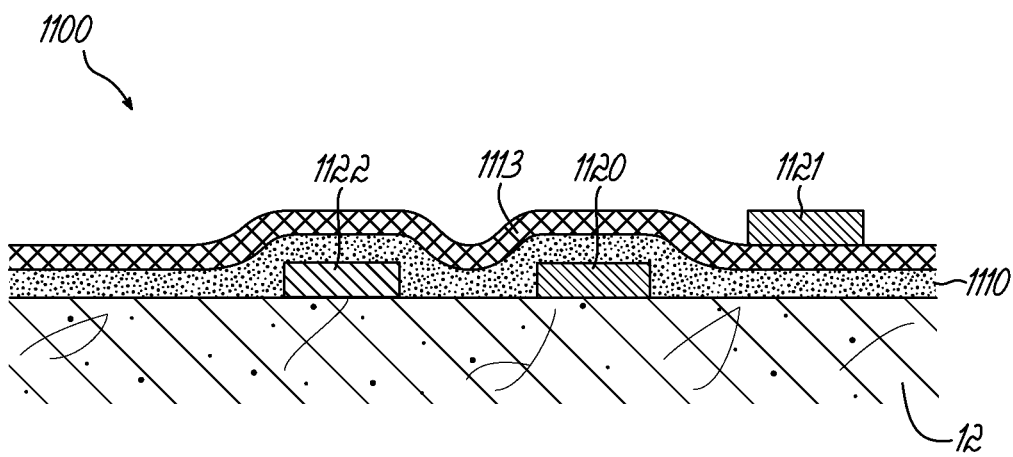
FIG. 11 is an elevation view of at least a portion of an example embodiment of the present invention sensor is capable of measuring the ability of the sweat to wick from the skin to a pump that is evaporative in nature and the sweat sampling rate is at least in part determined by the sensor measuring the ability for sweat to wick from the skin to a pump that is evaporative in nature.

With reference to FIG. 11, device 1100 includes sensor 1120, sensor 1121, electrode 1122, sweat porous adhesive 1110, and evaporative textile surface 1113. Device 1100 relies on evaporation to promote constant wicking of sweat from skin 12 to external evaporative textile surface 1113, where sensor 1121 is capable of measuring if the textile surface is saturated with external water or sweat and therefore reducing the sweat sampling rate, which could be used to determine the chronological assurance. Similar informing of chronological assurance was described for FIG. 7. In this way, effective sampling interval and therefore chronological assurance is further informed by more than just sweat generation rate at the skin, but also by flow rates through the device past the sensors. In some cases, the sampling interval and ability for the features to wick, absorb, or evaporate sweat could be predetermined, for example with use of the devices in a humid environment the known humidity is measured or incorporated by data entry, and along with a predetermined look-up table of the devices sampling interval vs. air humidity, could be used to further determine the chronological insurance. For example, some hydrogels will become partially hydrated in humid air and have a reduced sweat wicking rate from the onset, and in some arrangements, the flow of sweat or its solutes would be limited by the wicking rate of the gel.

The following examples are provided to help illustrate the present invention, and are not comprehensive or limiting in any manner

EXAMPLE 1

A sweat sensor patch with a predetermined sweat volume between the sensor and the skin is used by a football player who has a predetermined sweat generation rate that was previously artificially measured. A calculation of the chronological assurance is performed manually and inserted into the software controlling the sweat sensing system. The sweat sensing system then reports to the player's coach readings from the sweat sensor, such as: exertion level, hydration, muscle tissue damage, and an assurance of the sweat sampling rate of the sweat sensing system (chronological assurance). If, for example, the chronological assurance is 15 minutes, the coach can set his or her stop watch to 15 minute cycles as a reminder to check on sweat sensor readings from the player.

EXAMPLE 2

A neonate in critical condition is wearing a sweat sensing device and is being monitored for ammonia levels as an indicator of anaerobic activity. The device has an unknown sweat volume which is regularly measured using electrical impedance. The neonate is being stimulated to sweat using iontophoresis, and the sweat generation rate is estimated or predetermined in some way from a previous calibration test of sweat generation rates of similar neonates. The sweat sampling rate is then determined by the sweat sensing device, and, if sweat stimulation increases or decreases, the sweat generation rate is recalculated in the system. If the dead volume becomes too large because the device is peeling away from the skin, then an alarm sounds to let nurses know that the sweat monitoring system is no longer providing the chronological assurance needed to safely monitor changes in the neonate's condition.

EXAMPLE 3

A group of soldiers in a cold climate is attempting to secure a dangerous area in order to protect a group of civilians. The soldiers are using sweat monitoring systems to measure their physical and mental stresses through cytokine biomarker measurements. The soldiers are beyond their normal operating duration, and the commander is closely monitoring their conditions. The sweat sensor system for each soldier is measuring the sweat generation rate as it fluctuates and has a predetermined sweat volume and predetermined measurement of diffusion or contamination of solutes and biomarkers. The commander is provided with readings of the stresses on the soldiers and also a reading of the chronological assurance.

The commander sees the stress markers spike over a period of 30 minutes, and the chronological assurance is very low (for example, one hour). The commander knows that it is too late for an immediate intervention as the chronological assurance is low and determines to wait to see if the stress level stops increasing or levels off before making any decisions. The chronological assurance then increases dramatically to less than 10 minutes, suggesting that the exertion level is high, and the stress marker decrease. The commander can infer that the soldiers have accomplished their mission and are simply running back to their home position.

EXAMPLE 4

A transplant patient is taking an anti-rejection medication and is utilizing a sweat sensing device to monitor the drug levels in the body through the drug metabolites excreted in sweat. The patient is to wear the device 24 hours a day, replacing it only as needed. Because sweat stimulation can cause irritation, it is desired to keep the sweat stimulation at the minimum level needed for readings in 30 minute intervals. The sweat stimulation is auto-regulated by sweat generation rate. The rate of pilocarpine delivery is controlled in part by the flow of sweat out of the gland which is in the opposite direction of the pilocarpine delivery. In an advanced form, the sweat generation rate could be controlled at a fairly steady level by providing a predetermined concentration of pilocarpine exposed to the skin and again allowing simple diffusion of the pilocarpine through the sweat duct to receptors near the sweat gland, possibly even by changing that concentration of pilocarpine exposed to the skin by electrical or microfluidic transport between a reservoir of pilocarpine and the skin.

The chronological assurance could be predetermined or measured, in whole or in part, and the patch (1) could be designed with microfluidics, sweat volumes, and iontophoresis waveforms specifically to passively maintain and assure an appropriate sweat generation rate, or (2) in an alternate advanced form, the sweat generation rate could be measured by impedance, ion concentration, or other means, and the rate of pilocarpine delivery to the sweat gland would be controlled actively to adjust the sweat generation rate to the desired range. In either of these embodiments, a key aspect of chronological assurance is the patches passive or active regulation of the chronological assurance, which is more than simply reporting the current chronological assurance.

EXAMPLE 5

An emergency victim of an accident has been placed in an ambulance. The chronological assurance of a sweat sensing device patch is set by paramedics to a chronological assurance of 5 minutes, as the patient is in critical condition. Later, when the patient partially recovers to stable condition at the hospital, a nurse and doctor team decides to set the chronological assurance of the patch to 1 hour. The patch includes a green LED to indicate that the patch is providing the proper setting of chronological assurance and a red flashing LED to indicate when it is not.

EXAMPLE 6

A soccer player is wearing a sweat sensor patch mounted inside a tightly strapped shin-guard and is away from the sidelines and out of communication distance. The chronological assurance of the patch is recorded over time using data-logging electronics within the sweat sensor patch. When the soccer player reaches the sideline, she crosses over an RFID reader match which reads off the sweat measurement data along with the chronological assurance.

EXAMPLE 7

A runner wearing a sweat sensing patch has a music player with Bluetooth connectivity, which wirelessly obtains the chronological assurance from the sweat sensing patch and reports sweat measurements during interval training on a track. The music player then audibly provides the chronological assurance to the runner. The runner knows what time period the readings actually represent during the intervals. Because the patch measures sweat generation rate, the runner also becomes accustomed to obtaining peak chronological assurance by not under-dressing in cold weather.

EXAMPLE 8

A diver working on a deep sea oil-rig is wearing a sweat sensing device to measure oxygen toxicity. The worker has no access to an external display. The worker is alerted that the sweat sensing device is coming loose such that the chronological assurance is no longer within a safe window to warn the diver of oxygen toxicity. The warning could be provided by a piezoelectric vibrator or through a minor pulsating electrical stimulus, either of which can be contained in the sweat sensing device.

EXAMPLE 9

A person, who has regular night sweats, wants to measure his sleep quality. The night sweats can be utilized to determine chronological assurance which can then determine and report the quality of the sweat measured and reported data for sleep quality.

EXAMPLE 10

A mother giving birth has wireless sweat sensors placed at two or more locations on the body. Two or more sensors are utilized to provide the best possible chronological assurance to mitigate risk that chronological assurance would be falsely reported. Readings every few minutes of sweat and biomarkers representing biomarker concentrations in blood are critical to ensuring the safety and health of the mother.

EXAMPLE 11

A group of heavy equipment operators are all wearing sweat sensing patches on the same construction site. The hot weather conditions are affecting sweat generation rate. The workers are all being monitored for chronological assurance. A storm comes in and quickly cools the worksite. The chronological assurance from all of the workers increases from 15 minutes to 50 minutes on average. However, the chronological assurance from one worker remains at 15 minutes. This worker is identified to be excessively struggling with his equipment and is removed from duty thanks to the larger statistical data set. The headquarters for the construction firm also realizes that either effort level or weather has abruptly changed at the construction site as chronological assurance decreased and calls in to make sure there was not a work stoppage.

EXAMPLE 12

A cardiac patient is released from the hospital but is still at a high risk of another heart attack. A sweat sensing device is worn by the patient and utilizes a long sweat sampling interval and chronological assurance of 1 hour to check on biomarkers associated with a heart attack (troponin, creatine kinase, one of several cytokines, etc). One of these biomarkers is sensed at a level indicating a risk that a heart attack has occurred or may occur, and the chronological assurance of the sweat sensing device automatically and actively decreases to 10 minutes to allow a denser set of data for closer observation of the patient's health status. Heart rate, EKG, pulse-oxygen, or other known monitoring methods could be incorporated within the device or other devices worn by the patient to inform the chronological assurance needed for the device and actively control the chronological assurance of the device.

While the invention has been described in particularity and with reference to specific examples, the invention is not intended to be limited to such particulars. It will be appreciated by persons skilled in the art that various modifications can be made to the invention without departing from the scope thereof as defined in the appended claims.

What is claimed is:

1. A device, comprising:
   one or more sensors, wherein each sensor of the one or more sensors is configured to obtain a measurement of a characteristic of an analyte in sweat at a plurality of time periods;
   a sampling volume positioned between a sampling site and the one or more sensors, wherein the device is configured to route sweat samples from the sampling site, through the sampling volume to the sensors
   a controller configured to:
      define a sweat generation rate, wherein the sweat generation rate is an estimate of a volume of sweat per unit of time;
      define a sampling rate in which each sensor of the one or more sensors is configured to obtain a measurement of the characteristic of the analyte in a sweat sample of a plurality of sweat samples, the sampling rate being determined based on the sampling volume, the sweat generation rate, and a chronological assurance; and
      control each sensor of the one or more sensors such that measurements are obtained by the one or more sensors in accordance with the sampling rate.

2. The device of claim 1, wherein the controller uses the chronological assurance to modify the sampling rate such that measurements are obtained by each of the one or more sensors once per a time interval, the time interval beginning when a sweat sample of the plurality of sweat samples emerges from skin at the sampling site and ending when the sweat sample of the plurality of sweat samples reaches the one or more sensors.

3. The device of claim 1, wherein the controller uses the chronological assurance to modify the sampling rate such that each measurement obtained from a sensor of the one or more sensors is obtained using a different sweat sample of the plurality of sweat samples.

4. The device of claim 1, wherein the controller uses the chronological assurance to modify the sampling rate based on an advective flow rate, the advective flow rate being a rate in which a sweat sample of the plurality of sweat samples flows from the sampling site and to a sensor of the one or more sensors.

5. The device of claim 1, wherein the controller is further configured to:
   determine a distance from the sampling site to a sensor of the one or more sensors;
   detect an advective flow rate, the advective flow rate being a rate in which a sweat sample of the plurality of sweat samples flows from the sampling site and to a sensor of the one or more sensors, wherein a value of the chronological assurance is based on the advective flow rate and the distance; and
   modify the sampling rate using the chronological assurance such that the modified sampling rate causes each successive measurement to be obtained from a different sweat sample of the plurality of sweat samples.

6. The device of claim 1, wherein each sweat sample of the plurality of sweat samples flows in series to a sensor of the one or more sensors, and wherein the controller uses the chronological assurance to modify the sampling rate to prevent multiple measurements from being obtained by the one or more sensors from a same sweat sample.

7. The device of claim 1, wherein the controller uses the chronological assurance to modify the sampling rate to a rate that improves an accuracy of successive measurements obtained from the one or more sensors.

8. The device of claim 1, wherein the controller uses the chronological assurance to limit the sampling rate to a rate in which each subsequent measurement obtained by the one or more sensors uses a newer sweat sample than a previous measurement obtained by the one or more sensors.

9. The device of claim 1, wherein the controller is further configured to:
   detect a sensor response interval, the sensor response interval being an interval between a moment the sweat sample reaches a sensor and a moment the sensor completes a measurement; and
   modify the sampling rate such that measurements are obtained by each of the one or more sensors once per a time interval, the time interval beginning when a sweat sample of the plurality of sweat samples emerges from skin at the sampling site and ending when the sweat sample of the plurality of sweat samples reaches the one or more sensors and the sensor response interval lapses.

10. The device of claim 1, wherein the chronological assurance decreases the sampling rate.

11. A device, comprising:
one or more sensors, wherein each sensor of the one or more sensors is configured to obtain a measurement of a characteristic of an analyte in sweat at a plurality of time periods;
a sampling volume positioned between a sampling site and the one or more sensors, wherein the device is configured to route sweat samples from the sampling site, through the sampling volume and to the sensors;
a controller configured to:
define a sweat generation rate, wherein the sweat generation rate is an estimate of a volume of sweat per unit of time;
define a sampling interval over which each sensor of the one or more sensors is to obtain a measurement of the characteristic of the analyte in a sweat sample of a plurality of sweat samples, the sampling interval being determined based on the sampling volume, the sweat generation rate, and a chronological assurance; and
control each sensor of the one or more sensors such that measurements are obtained by the one or more sensors in accordance with the sampling interval.

12. The device of claim 11, wherein the chronological assurance causes the sampling interval to begin when a sweat sample of the plurality of sweat samples emerges from skin and end when the sweat sample of the plurality of sweat samples reaches the one or more sensors.

13. The device of claim 11, wherein one measurement is obtained from a sensor of the one or more sensors during each sampling interval.

14. The device of claim 11, wherein the controller uses the chronological assurance to modify the sampling interval based on an advective flow rate, the advective flow rate being a rate in which a sweat sample of the plurality of sweat samples flows from the sampling site and to a sensor of the one or more sensors.

15. The device of claim 11, wherein the controller is further configured to:

determine a distance from the sampling site to a sensor of the one or more sensors;
detect an advective flow rate, the advective flow rate being a rate in which a sweat sample of the plurality of sweat samples flows from the sampling site and to a sensor of the one or more sensors, wherein the chronological assurance is based on the advective flow rate and the distance; and
modify the sampling interval based on the chronological assurance such that measurements obtained from a sensor of the one or more sensors during a first sampling interval are obtained using a different sweat sample from measurements obtained from the sensor of the one or more sensors during a second sampling interval.

16. The device of claim 11, wherein each sweat sample of the plurality of sweat samples flows in series to a sensor of the one or more sensors, and wherein the controller uses the chronological assurance to modify the sampling interval such that during each sampling interval measurements are obtained by the one or more sensors from one sweat sample.

17. The device of claim 11, wherein the controller uses the chronological assurance to modify the sampling interval to an interval that improves an accuracy of measurements obtained from the one or more sensors.

18. The device of claim 11, wherein the controller uses the chronological assurance to increase the sampling interval.

19. The device of claim 11, wherein the controller uses the chronological assurance to increase the sampling interval such that each measurement obtained from a sensor of the one or more sensors during a sampling interval use newer sweat samples than each measurement obtained from the sensor of the one or more sensors during a previous sampling interval.

20. The device of claim 11, wherein the controller is further configured to:
detect a sensor response interval, the sensor response interval being an interval between a moment the sweat sample reaches a sensor and a moment the sensor completes a measurement; and
modify the sampling interval to begin when a sweat sample of the plurality of sweat samples emerges from skin at the sampling site and end when the sweat sample of the plurality of sweat samples reaches the one or more sensors and the sensor response interval lapses.

* * * * *

UNITED STATES PATENT AND TRADEMARK OFFICE
CERTIFICATE OF CORRECTION

| | |
|---|---|
| PATENT NO. | : 10,888,244 B2 |
| APPLICATION NO. | : 16/192862 |
| DATED | : January 12, 2021 |
| INVENTOR(S) | : Jason Charles Heikenfeld |

It is certified that error appears in the above-identified patent and that said Letters Patent is hereby corrected as shown below:

On the Title Page

Page 3, Column 1, Line 40, "Applictin" should be --Application--.

Page 3, Column 2, Lines 42-43, "International International Bureau, Notification Concerning Transmittal of International Preliminary Report on issued in International Application" should be --International Bureau, Notification Concerning Transmittal of International Preliminary Report on Patentability issued in International Application--.

Page 3, Column 2, Line 71, "Tectiles:" should be --Textiles:--.

In the Specification

Column 4, Lines 6-7, "sensor is capable of" should be --sensor which is capable of--.

Column 6, Lines 51-55, "The maximum stimulated sweat generation rate according to Buono 1992, J. Derm. Sci. 4, 33-37, "Cholinergic sensitivity of the eccrine sweat gland in trained and untrained men", the maximum sweat generation rate by pilocarpine stimulation are about" should be --According to Buono 1992, J. Derm. Sci. 4, 33-37, "Cholinergic sensitivity of the eccrine sweat gland in trained and untrained men", the maximum sweat generation rate by pilocarpine stimulation is about--.

Column 7, Line 15, "require a 10 minutes" should be --require 10 minutes--.

Column 7, Line 59, "the somewhere between" should be --somewhere between--.

Column 10, Line 17, "100 glands)=2.5 min Therefore," should be --100 glands)=2.5 min. Therefore,--.

Column 11, Line 26, "at which the point the device" should be --at which point the device--.

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,888,244 B2

Column 11, Line 53, "the number of sweat glands are measured" should be --the number of sweat glands is measured--.

Column 13, Line 50, "provide an impedance" should be --provides an impedance--.

Column 16, Line 12, "in any manner Alternate embodiments" should be --in any manner. Alternate embodiments--.

Column 18, Line 36, "insurance." should be --assurance.--.

Column 19, Line 37, "decrease." should be --decreases.--.

Column 21, Line 37, "etc)." should be --etc.).--.

In the Claims

Column 21, Line 63 (Claim 1), "to the sensors" should be --to the sensors;--.

Column 24, Line 31 (Claim 19), "use newer" should be --uses newer--.